United States Patent [19]

Stache et al.

[11] Patent Number: 5,608,093

[45] Date of Patent: Mar. 4, 1997

[54] CORTICOSTEROID 17-ALKYL CARBONATE 21-[0]-CARBOXYLIC AND CARBONIC ESTERS, AND PHARMACEUTICALS CONTAINING THESE COMPOUNDS

[75] Inventors: Ulrich Stache, Hofheim; Hans-Georg Alpermann, Königstein; Walter Dürckheimer, Hattersheim; Manfred Bohn, Hofheim, all of Germany

[73] Assignee: Hoechst Aktiengesellschaft, Frankfurt am Main, Germany

[21] Appl. No.: 294,804

[22] Filed: Aug. 25, 1994

[30] Foreign Application Priority Data

Aug. 27, 1993 [DE] Germany .................. 43 28 819.7

[51] Int. Cl.$^6$ .................. C07J 5/00; C07J 43/00; A61K 31/56

[52] U.S. Cl. .................. 552/601; 540/107; 540/108; 540/111; 540/112; 540/113; 540/114; 552/588; 552/595

[58] Field of Search .................. 552/610, 588, 552/595, 601; 540/107, 108, 111, 112, 113, 114; 514/177, 180, 181

[56] References Cited

U.S. PATENT DOCUMENTS

| | | | |
|---|---|---|---|
| 4,242,334 | 12/1980 | Stache et al. | 424/243 |
| 4,242,344 | 12/1980 | Lumma | 424/251 |
| 4,377,575 | 3/1983 | Stache et al. | 424/243 |
| 4,655,971 | 4/1987 | Page et al. | 552/574 |
| 4,948,533 | 8/1990 | Braughler et al. | 552/576 |

FOREIGN PATENT DOCUMENTS

| | | | |
|---|---|---|---|
| 0470617 | 2/1992 | European Pat. Off. | C07J 31/00 |
| 2735110 | 2/1979 | Germany . | |

OTHER PUBLICATIONS

CA 90 : 204370 (Feb. 15, 1979 Stache De 2735110).

M. Isogai et al., "Binding Affinities of Memtasone Furoate and Related Compounds Including Its Metabolites for the Glucocorticoid Receptor of Rat Skin Tissue," J. Biochem. Steroid Molec. Biol., vol. 44, No. 2, pp. 141–145, 1993.

Primary Examiner—Shean C. Wu
Attorney, Agent, or Firm—Finnegan, Henderson, Farabow, Garrett & Dunner, L.L.P.

[57] ABSTRACT

Corticoid 17-alkyl carbonate 21-carboxylic and carbonic esters of the formula I

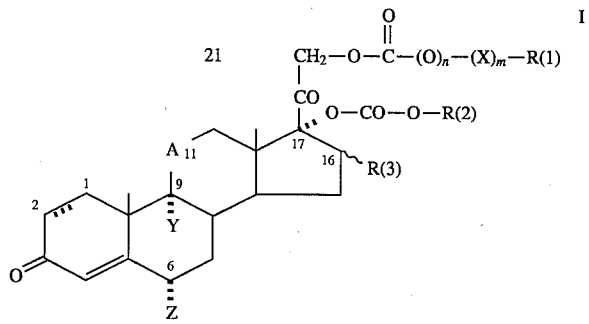

are described in which A is CHOH and CHCl, $CH_2$, C=O or 9(11) double bond; Y is H, F or Cl; Z is H, F or $CH_3$; R(1) is aryl or hetaryl; n and m are zero or 1; R(2) is alkyl or —$(CH_2)_2$—$OCH_3$; R(3) is H or methyl. They are obtained by reacting a compound of the formula II,

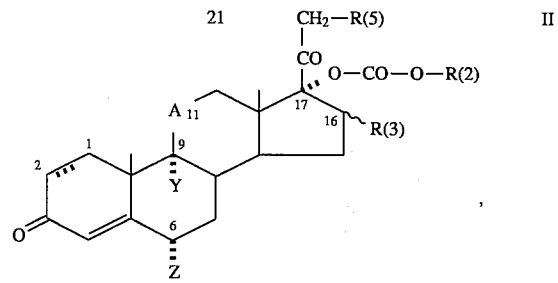

in which R(5) is OH, with an activated carboxylic acid of the formula III,

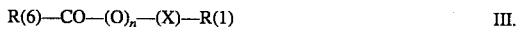

R(6)—CO—(O)$_n$—(X)—R(1)   III.

The compounds I have a very strong local and topical antiinflammatory action and exhibit a very good ratio of local to systemic antiinflammatory effects, which ratio is often markedly superior to that of analogous corticoid 17-alkyl carbonate 21-esters which do not carry any aryl or heteraryl group in the 21-ester radical.

4 Claims, No Drawings

CORTICOSTEROID 17-ALKYL CARBONATE 21-[0]-CARBOXYLIC AND CARBONIC ESTERS, AND PHARMACEUTICALS CONTAINING THESE COMPOUNDS

The invention realtes to corticoid 17-alkyl carbonate 21-carboxylic and carbonic esters of the Formula I

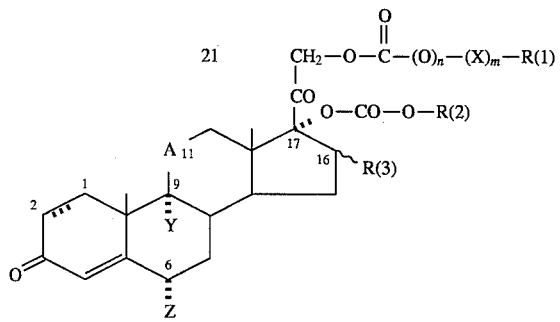

in which:

A is CHOH and CHCl in arbitrary steric arrangement, $CH_2$, C=O or 9(11) double bond, Y is hydrogen, fluorine or chlorine, Z is hydrogen, fluorine or methyl, R(1) is optionally substituted or fused aryl or hetaryl, X is (Cphd $1-C_4$)-aliphatic hydrocarbon, saturated, unsaturated once or more than once, branched by alkyl groups, or is ($C_1-C_4$)-hydrocarbon, unsubstituted or inserted or substituted by heteroatoms O, S or N, n is zero or 1, m is zero or 1, R(2) is linear or branched ($C_1-C_8$)-alkyl or $—(CH_2)_2—OCH_3$, R(3) is hydrogen or α- or β-methyl.

Corticoid 17-alkyl carbonate 21-carboxylic and carbonic esters of the Formula I are preferred in which:

R(1), A, Y, Z and R(3) are defined as above,

R(2) is linear or branched ($C_1-C_5$)-alkyl or $(CH_2)_2—OCH_3$.

The invention also realtes to a process for preparing a compound I, in which process a) a compound of the Formula II,

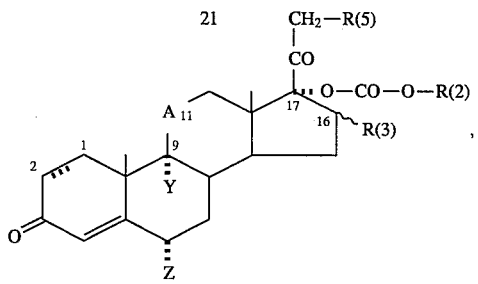

in which R(5) is OH and the remaining substituents have the abovementioned meanings, a 1) is reacted with an activated carboxylic acid of Formula III, preferably a halide or anhydride or azolide,

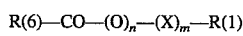

where:

n is zero, m is zero or 1, and x and R(1) have the abovementioned meanings, and

R(6) is Cl, Br, $O[—CO—(O)_n—(X)_m—R(1)]_1$, $—O—C(O)CF_3$, or another activated acid radical, a 2) is reacted with a haloformate of Formula III, in which n is 1, m is zero or 1, X and R(1) have the abovementioned meanings, and R(6) is Cl, Br or I, or a (3 is reacted with a carboxylic acid of the Formula III itself, in which R(6) is OH, and n is zero, and the other substituents are given in Formula III, in the presence of water-eliminating reagents (DCCI, etc.), or in which b) compounds of the Formula II,

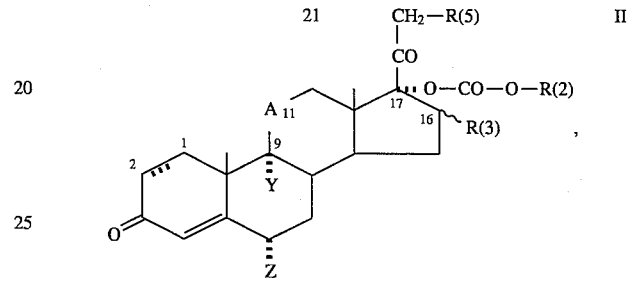

in which R(5)=Br, I or a sulfonic aryl or alkyl ester group, and the remaining substituents have the meanings given in Formula I, is reacted with a salt, preferably K or Na salt, or a trialkylammonium salt, of a carboxylic acid of the Formula III,

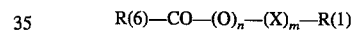

in which

R(6) is $—[O^-Me^+]$, and n is zero, and the remaining substituents have the meanings given in Formula III, where Me is preferably the cation of an alkali metal salt or of a trialkylammonium salt.

The steroid-17-alkylcarbonates having a free 21-hydroxyl group of the Formula II [R(5)=OH], which are required as starting compounds, are prepared by the processes of U.S. Pat. No. 4,242,334 (HOE 77/F 154) and EP-A 470 617 (HOE 90/F 241).

The steroid-17-alkylcarbonates in which R(5) is Br, I, $—OSO_2$-aryl or $—OSO_2$-alkyl in Formula II are prepared in accordance with U.S. Pat. No. 4,377,575 (HOE 78/F 082) and EP-A-470 617 (HOE 90/F 241). In this context, the 17-alkyl carbonates of the following corticosteroids are suitable:

Prednisolone, prednisone, 6α-methylprednisolone, 6α,16α-dimethylprednisolone, 16α-methylprednisolone, hydrocortisone (cortisol), cortisone, 6α-methylcortisol, Reichstein's "substance S", 11-desoxy-9(11)-dehydro-prednisolone, 6α-fluoroprednisolone, dexamethasone, 6α-fluorodexamethasone, 9α-fluoroprednisolone, 6α,9α-difluoroprednisolone, 6α-methyl, 9α-fluoroprednisolone, betamethasone, clobetasol.

The carboxylic acids of the Formula III [R(6) is OH and n is zero], or their activated derivatives, such as the halides [R(6)=Cl, Br, or I], or their anhydrides, or their azolides [R(6) is imadazolide or triazolide], or their salts [R(6) is (MeO)—, preferably (KO)— or (NaO)—], which are employed as reaction partners are known as a rule and are prepared, where appropriate, by commonplace preparative methods. Examples of carboxylic acids in accordance with Formula III [R(6) is OH and n is zero] which can be employed in accordance with the invention are to be found in the list at the end of the text prior to the claims.

All the carboxylic acids belonging in this category carry, in their acid radical, an aryl or hetaryl group which is optionally substituted by halogen, alkyl, alkoxy, acyl, thioalkyl or thioacyl, nitro, amino, aminoalkyl, amido, cyano, oxyacyl, oxaryl, etc., and also optionally fused. The aryl and hetaryl groups are essential constituents of the invention.

The dotted line between carbon atoms 1 and 2 indicates that this bond can be a single bond or an unsaturated bond.

As is shown in the pharmacological section, the quality of the effect demonstrated by corticoid 17-alkyl carbonate 21-carboxylic esters of this type (=21-aryl or 21-hetaryl ester type), in particular, is often clearly superior, as regards the relationship between local and systemic anti-inflammatory effects, to that of structurally related corticoid 17-alkyl carbonate 21-carboxylic esters which do not carry any aryl or hetaryl group in the 21-acid radical.

Detailed description of the conduct of the individual reactions in the processes for preparing the process products according to Formula I in accordance with the invention:
regarding process variant a:
in order to prepare 21-carboxylic esters of the abovementioned type, either carbonyl halides or carboxylic azolides of the Formula IV

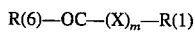

in which:
R(6) is Cl, Br, I,

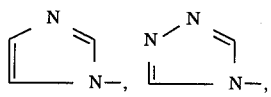

m is zero or 1, and

R(1) and X have the meanings given for Formula III, or carboxylic anhydrides of the Formula V

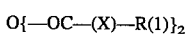

in which:
m is zero or 1, and

R(1) and X have the meanings given for Formula III, are preferably used. In both cases, the carboxylic acids on which they are based and which are included in the list, preferably their carbonyl chlorides and carboxylic anhydrides and imidazolides or triazolides, are used.

R(6) in Formula IV can also comprise other groups which activate the carboxyl group in carboxylic acids for esterification, such as, for example, —O—CO—CF$_3$, or the activated carboxylic acids which can be prepared from phosphonic or phosphinic anhydrides (e.g. propanephosphonic anhydride or polyphosphoric anhydride (PPA)).

Additional phosphorus reagents which can bring about mild esterification of organic carboxylic acids with the 21-alcohol group of corticoid-17-alkylcarbonates are listed or described in the literature references Synth. Commun. 13, 471ff (1983) and Synth. Commun. 14,515ff (1984).

In order to carry out the esterification using a carbonyl halide or carboxylic anhydride or a haloformate, the steroid component is dissolved in an inert solvent, for example in an ether, such as dioxane, tetrahydrofuran or diglyme, or optionally halogenated hydrocarbons, such as benzene, toluene, cyclohexane, methylene chloride or chloroform, or in acetone or in a mixture of these solvents. In order to remove the hydrohalic acid which is produced in the reaction, 1–1000 molar equivalents of a tertiary base, such as pyridine, quinoline, triethylamine, dimethylaniline, dimethylaminopyridine, etc., are added. However, an inorganic base, such as sodium hydrogen carbonate or calcium carbonate, can also be used for removing the acid. 1–200 molar equivalents, preferably 1–3 molar equivalents, of one of the above-listed acylating agents, optionally dissolved in one of the above-listed solvents, are then added dropwise at a temperature of −40° C. to the boiling point of the solvent used, preferably at a temperature of 0° C. to 25° C. Subsequently, the reaction mixture is left to stand for 1 to 120 hours at a temperature of −40° C. up to the boiling point of the solvent, preferably at a temperature of 0° C. to 25° C.

When using carboxylic anhydrides as acylating agents, it is now and then advantageous not to add solvents. As a rule, it is sufficient simply to add the organic base, preferably pyridine, to the acid anhydride, which may optionally be used in excess.

Particularly in the case of sensitive (and sometimes unstable) carboxylic acid derivatives of the above-mentioned type, in particular when using phenylacetyl chlorides or anhydrides and hetarylacetyl chlorides and anhydrides, it is of great preparative advantage, and of great advantage with regard to the selectivity of the reaction, if the corticoid-17-alkylcarbonates having a free 21-hydroxyl group are reacted with 1–4 molar equivalents of the chloride or anhydride at −10° to +6° (maximally 20° C.) in chlorinated hydrocarbons, such as, preferably, dichloromethane, and with 1–4 molar equivalents of a pyridine base, preferably dimethylaminopyridine.

Under these circumstances, the reaction products of the formula I are obtained in high purity, with negligible quantities of byproducts, in particular 11-acylated products (monitoring of the course of the reactions with TLC), that is the reactions are highly regioselective with regard to conversion of the 21-hydroxyl group.

In the case of the reactions with carbonyl chlorides, absolute dioxane or tetrahydrofuran is frequently advantageously added to the reaction mixture, e.g. in the case of benzoyl chloride, where the ratio of dioxane/pyridine is 1:1; in addition, in order to accelerate the reaction, the reaction mixture is often, particularly in the case of sterically hindered or less reactive carbonyl chlorides or carboxylic anhydrides, heated at about 60° C. (monitoring of the course of the reaction with TLC).

The reaction products can be characterized using thin layer chromatography (TLC); in this context, the reaction products have $R_F$ values of about 0.65–0.8. As a rule, the reaction products are characterized by mass spectra using MS=m/z=... (M+H$^+$) (FAB spectra, as a rule); the monoisotopic molar masses are registered in each case. The M+H$^+$ values were rounded up in each case. IR spectra, $^1$H-NMR spectra and UV spectra can also be enlisted for the characterization.

For the working up, the reaction mixture is poured into water, to which sodium chloride and sodium bicarbonate may, where appropriate, have been added, in association with which the reaction products generally precipitate out in crystalline form, frequently only after standing for some length of time. Oily or waxy reaction products are concentrated by extracting, while shaking, with a suitable extracting agent, and then evaporating. If necessary, the reaction products can be fractionated or purified by recrystallization or by chromatography. Intensive digestion in an organic solvent which either does not dissolve the reaction product or else dissolves it as little as possible, for example diethyl ether or cyclohexane, or a mixture of these components, may frequently suffice for the further purification of the reaction products.

When using carboxylic azolides, the esterification is expediently carried out as a one-pot reaction. In this case, arylacetic acid or hetarylacetic acid, for example, or another carboxylic acid of the formula III [R(6) is OH, n is zero], is dissolved in absolute pyridine, and a preferably equimolar quantity of N,N-carbonyldiimidazole or N,N-carbonyldi-[1H-1,2,4-triazole] is added, with the corresponding acid azolides forming at 0°–20°. After adding an approximately equimolar quantity of corticoid-17-alkylcarbonate of the formula II [R(5)=OH] and a catalytic quantity of a base, preferably sodium hydride or sodium imidazolide, the mixture is stirred in pyridine at between 0° and 40° C., preferably 20°, and then worked up in the customary manner.

However, the carboxylic azolide, which has previously been prepared in absolute tetrahydrofuran with equimolar quantities of N,N'-carbonylazolide and carboxylic acid, and then isolated, can also be added to the steroid dissolved in solvents such pyridine, dimethylformamide or tetrahydrofuran, with the subsequent procedure being as described above [see also Chem. Ber.95, pp. 1284 ff. (1962)].

When esterifying with the aid of phosphonic or phosphinic anhydrides, equimolar quantities of carboxylic acid and corticoid-21-alcohol in absolute pyridine are preferably added to 50% strength propanephosphoric anhydride in methylene chloride at 20° to 60° C. while also adding 4-dimethylaminopyridine as an acid-capturing agent, with the working up being carried out as usual (pouring into ice water, extracting with ethyl acetate, washing with 5% $KHSO_4$, distilling off and crystallizing). Polyphosphoric anhydride (PPA) may also be employed instead of phosphonic anhydrides.

An additional advantageous esterification process, which is applicable to the carboxylic acids according to formula III [R(6) is OH and n is zero] or included in the list, is the direct reaction of corticoid-17-alkylcarbonates of the formula II [R(5) is OH] using water-removing agents such as carbodiimides, preferably N,N'-dicyclohexylcarbodiimide (DCC). In some cases, "molecular sieves" can also be used as water-removing agents in place of DCC.

The esterification can be catalytically accelerated or optimized by adding an acid, e.g. sulfuric acid, phosphoric acid, hydrochloric acid, diphenylphosphoric acid or p-toluene sulfonic acid, or their pyridinium salts, or an organic base, such as, for example, dimethylaminopyridine (=particularly advantageous in halogenated solvents, such as, for example, methylene chloride, or in dimethylformamide), something which is very advantageous, particularly in the case of carboxylic acids, e.g. of the indolylacetic acid, pyrrolecarboxylic acid, arylacetic acid and hetarylacetic acid types, etc., which are either sensitive or otherwise only react with difficulty. In this context, it is surprising that the secondary 11-hydroxyl group in the corticoid-17-alkylcarbonates which are employed is not as a rule concomitantly esterified simultaneously, as is occasionally observed when esterifying with the corresponding acid halides.

In a particular variant of the process, a catalytic quantity of the pyridinium salt of sulfuric acid is added to a solution of one molar equivalent of corticoid 17-alkyl carbonate 21-alcohol [formula II, R(5) is OH] and 1–4 molar equivalents, preferably two equivalents, of carboxylic acid of the formula III [R(6) is OH and n is zero] in absolute pyridine, and this is followed, after about 20 min., by the addition of 1–4 molar equivalents, preferably 1–2 molar equivalents, of dicyclohexylcarbodiimide. The mixture is then stirred at 0°–50° C., preferably 20° C., until a sample examined by TLC indicates that the starting carboxylic acid has disappeared and that only desired carboxylic acid-21-corticoid esters of the formula I are present. The dicyclohexylurea which has formed is filtered off and the filtrate is then expediently poured into water; this is then followed by filtration (in the case of crystal formation) or decantation (in the case of oily or waxy precipitates), washing with water (where appropriate, extraction can also take place with extracting agents, in particular dichloromethane), drying, and recrystallization as usual; alternatively, if required, the reaction products are purified by customary chromatography, preferably on silica gel.

Instead of pyridine, other inert solvents, such as, for example, tetrahydrofuran, dioxane, methylene chloride or dimethylformamide, expediently with the addition of tertiary bases, for example pyridine or 4-dimethylaminopyridine, can also be used in some cases. The latter solvents are to be preferred when molecular sieves are used as water-removing agents.

In addition to this, the following variant has proved valuable for esterifying with the sensitive arylacetic acids and heterylacetic acids: 1 equivalent of carboxylic acid is dissolved at 0° C. in absolute dichloromethane, and 1 equivalent of DCCI, 0.2 equivalent of 4-N,N'-dimethylaminopyridine and a solution of one equivalent of corticosteroid 17-alkyl carbonate 21-alcohol in absolute dichloromethane are then added in succession and the mixture is stirred at 20° C. for 18 to 48 hours. After the customary working up, the desired ester of the formula I can be obtained in pure form. A molecular sieve can be used instead of DCCI.

In a further esterification method, 1 molar equivalent of carboxylic acid and trifluroacetic anhydride are added to corticoid 17-alkyl carbonate 21- [tert-butyldimethylsilyl-(O)-ether] in absolute tetrahydrofuran, and the customary working up takes place after stirring at 20° C. for about 1–6 hours.

However, the carboxylic acid and the corticoid 17-alkyl carbonate 21-alcohol (free form) can also be reacted directly with trifluoroacetic anhydride to give the desired 21-carboxylic ester (=formation of the mixed anhydride from carboxylic acid and trifluoroacetic acid, which anhydride then reacts with the 21-alcohol to give the 21-ester).

Regarding process variant b:

A further advantageous process variant, which leads to the corticoids according to the invention, comprises heating a corticoid 17-alkyl carbonate 21-halide, preferably 21-iodide or 21-bromide, or 21-sulfonate, preferably 21-p-chlorobenzene sulfonic ester or 21-methane sulfonic ester, with the metal salts, preferably alkali metal salts or trialkylammonium salts, of the carboxylic acids included in list 2, in inert organic solvents, preferably dimethyl sulfoxide, dimethylformamide, 2-butanone, acetone or acetonitrile, at 20° C. up to the boiling points of the solvents used, preferably at about 50° C., for 1–16 hrs., preferably 1–10 hrs., and isolating after the customary working up, preferably pouring in water, filtering or decanting off the precipitate, and customary purification.

In connection with this nucleophilic reaction in which a 21-halide or 21-sulfonic ester group is exchanged for a carboxylic ester group, it is surprising that, under the preferably alkaline reaction conditions, the 17-alkylcarbonate group, which is jointly responsible for the activity profile, is not simultaneously saponified in the process products.

The compounds I prepared according to procedures a) and b) are such that a hydroxyl group in the 11 position can, where appropriate, be oxidized to the keto group by customary methods. This oxidation is preferably carried out using chromium trioxide in an acid medium and in an inert organic solvent. A 9(11) double bond which is present in the corticoid moiety can, where appropriate, be converted by adding hydrohalic acid or by chlorine, in accordance with the usual known methods, into the corresponding corticoid 17-alkyl carbonate 21-esters having a 11β-hydroxyl, 9α-halide group (9αF, Cl) or 11β,9α-dichloro group.

The process products possess valuable pharmacological properties. They have, in particular, a very strong local and topical antiinflammatory action, and some of them exhibit, surprisingly, a very good ratio of local to systemic antiinflammatory effect, which ratio is often markedly superior, as can be deduced from pharmacological standard tests (see pharmacological test section), to that of analogous corticoid 17-alkyl carbonate 21-esters which do not carry any aryl or hetaryl group in the 21-ester radical, such as, for example, 21-ester groups having a 21-alkyl group. Accordingly, an agent for treating inflammatory dermatoses and comprising a compound of the formula I is also a subject of the invention.

The process products can be used in veterinary and human therapy in the form of suspensions, ointments, creams, sprays, etc., for treating inflammatory dermatoses of a wide variety of origins. In this context, it is to be emphasized as being particularly advantageous for the local and topical forms of therapy that, owing to their extremely favorable ratio of local to systemic anti-inflammatory effect, even in the case of lengthy therapy at high dosage rates, the process products are able in practice only to elicit trivial systemic side effects. In the case of external treatment, ointments, creams, suspensions, etc., are used at a concentration of 0.01 to 2% by weight. In particular, the process products exhibit a split (ratio) of local/systemic antiinflammatory effects in pharmacological tests which is to some extent appreciably better than that of corresponding preparations having a 21-ester group lacking aryl or hetaryl moieties, as are found in the compounds according to the invention, in the ester portion. In addition, some of the process products also exhibit a more powerful local antiinflammatory action than do the abovementioned analog preparations. In addition to this, the corticoid 17-alkyl carbonate 21-esters according to the invention can often have a still lower atrophodermatogenicity than do the abovementioned analogous corticoid-17-alkylcarbonate derivatives, which is a further advantage for their use in dermatotherapeutic treatment.

Corticoid 17-alkyl carbonate 21-cinnamic esters, in particular those substituted in the 4 position in the aromatic moiety by methoxy, methylenedioxy or ethoxy, as well as corticoid 17-alkyl carbonate 21-[4-(dimethylamino)benzoate], can, by way of their antiinflammatory effect, possess an additional sun-screen effect against solar radiation, in particular UV-B and UV-A radiation. Furthermore, corticoid-17-alkylcarbonates having a chlorambucil moiety in the 21-ester, as, for example, prednisolone 17-ethyl carbonate 21-chlorambucil ester, can have antitumorigenic effects which correspond to the effects of the known prednimustine (Merck Index 11, 7718).

In addition to this, the process products according to the invention can be combined in pharmaceutical formulations with diverse antibiotics which are locally active and which are well tolerated by the skin, e.g. of the gentamycin, neomycin, erythromycin or tetracycline type, or of the fusidic acid type, and others. Such combinations of the process products and the locally active antibiotics can be used for treating primary bacterial, or bacterially superinfected, inflammatory dermatoses.

Pharmacological experimental section

Thus, prednisolone 17-ethyl carbonate 21-phenylacetic ester (I) or betamethasone 17-ethyl carbonate 21-phenylacetic ester (II), for example, exhibited a strong local antiinflammatory effect in association with a strikingly favorable split to weak systemic activity, as is evident from the pharmacological test results recorded below [preparation for comparison, prednicarbate (=prednisolone 17-ethyl carbonate 21-propionate (U.S. Pat. No. 4,242,334) and (Merck Index 11, 7717))]:

1. Local antiinflammatory effect in rat croton oil ear edema following epicutaneous application We used the rat ear method of Tonelli et al.: male Wistar rats from our own colony and weighing about 50 g were treated epicutaneously on the right ear with the irritant or with irritant containing test substance. The left ear remained untreated. TPA (12-O-tetradecanoylphorbol 13-acetate, SIGMA P 8139) dissolved in acetone, 0.4 mg/ml, (of which 20 µl each on the inside and outside) was used for eliciting the inflammation. The corticoids under examination were dissolved in this solution in the given final concentrations. Controls only received the TPA/solvent mixture. The animals were sacrificed using $CO_2$ 4 h after the epicutaneous treatment. Disks measuring 8 mm in diameter were punched out of the right (treated) and the left (untreated) ears and weighed immediately. This difference, as the parameter for the degree of inflammation, was set at 100 in the controls (mg, x±s). The antiinflammatory effect is characterized by giving the dose in mg/ml which is required for approximately 50% inhibition:

| Treatment | mg/ml | x ± s (mg) | Inhibition in % |
| --- | --- | --- | --- |
| Control | | 15 ± 5.2 | — |
| Compound I | 0.03 mg/ml | 10 ± 3.0 | 33 |
| Compound I | 0.1 mg/ml | 5 ± 1.1 | 67 |
| Compound I | 0.3 mg/ml | 3 ± 2.3 | 80 |
| Compound II | 0.1 mg/ml | 5.1 ± 3.3 | 66 |
| Compound II | 0.3 mg/ml | 4.5 ± 3.1 | 70 |
| Prednicarbate | 1 mg/ml | 3 ± 1.7 | 80 |

Result

Compound I is approximately three times more powerful than prednicarbate,

Compound II has a corresponding effect to that of compound I 2 a) Examining for systemic antiinflammatory effect in the "antiinflammatory effect following subcutaneous administration: carrageenan paw edema in rats" test.

The carrageenan paw edema test in rats in accordance with the method described by Winter et al. Proc. Soc. Exp. Biol. (New York) Volume 111, p. 544 (1962) was chosen as the test for the acute systemic antiinflammatory effect. Male Sprague-Dawley rats of about 120 g in weight were given the substances to be tested s.c. (0.2 ml/100 g) dissolved in sesame oil. 30 min later, 0.1 ml of a 0.5% carrageenan solution was injected into the left hind paw. 6 h later, the degree of swelling was measured volumetrically. Controls were only given sesame oil.

The paw volumes are given in ml, x±s. In this case too, the antiinflammatory effect is characterized by giving the dose in mg/kg required for approximately 50% inhibition.

| | Dose in mg/kg s.c. | Starting value (ml) x ± s | Increase in volume (ml) (x ± s) |
|---|---|---|---|
| Control | Sesame oil | 1.44 ± 0.09 | 0.57 ± 0.07 |
| Compound I | 0.3 | 1.42 ± 0.04 | 0.34 ± 0.12 |
| | 3.0 | 1.38 ± 0.06 | 0.19 ± 0.9* |
| Compound II | 0.3 | 1.42 ± 0.07 | 0.33 ± 0.12 |
| | 3.0 | 1.38 ± 0.06 | 0.19 ± 0.9* |

For both preparations, significant systemic effects (*$p<0.05$, Dunnett's test), measured as inhibition of the paw edema, only appear after a dose of 3 mg/kg. This corresponds to the behavior of prednicarbate.

2 b) Examining for systemic effect: gluconeogenesis in rats

A sensitive method for detecting systemic effects on carbohydrate metabolism is to examine the gluconeogenic effect of corticosteroids in the adrenalectomized rat. Three days prior to the experiment, groups of in each case 6 rats are adrenalectomized under pentobarbital anesthesia and then provided with 0.9% sodium chloride solution as drinking fluid. Two days later, i.e. 24 hours before initiating the experiment, the feed is removed in order to reduce the glycogen stores in the liver.

On the day of the experiment, the preparations under examination are administered subcutaneously, dissolved in sesame oil (2 ml/kg). Six hours later, the animals are decapitated, and in each case the liver is removed and 1 g thereof is taken up in 5 ml of 0.6 molar perchloric acid. After homogenization, the free glucose is measured in the supernatant from the centrifugation, while the centrifugation sediment (centrifugate; glycogen) is cleaved enzymatically with amyloglucosidase, after which the glucose content is also measured in this fraction (Hexokinase method, Boehringer Mannheim). The following results were obtained:

| Treatment | Dose (mg/kg s.c.) | Liver glycogen | Glycogen + glucose mg/100 g of liver |
|---|---|---|---|
| Control I | Sesame oil | 0.5 ± 0.3 | 8.9 ± 1.2 |
| Prednicarbate | 0.3 | 1.0 ± 1.7 | 19.3 ± 4.3 |
| Prednicarbate | 3 | 111 ± 46* | 170 ± 46* |
| Compound I | 0.3 | 0.5 ± 0.7 | 11.3 ± 2.0 |
| Compound I | 3 | 2.4 ± 2.4 | 25.9 ± 13 |
| Control II | Sesame oil | 2.4 ± 0.5 | 14.1 ± 3.6 |
| Compound II | 0.3 | 2.8 ± 1.4 | 23.6 ± 6.8 |
| Compound II | 3 | 7.4 ± 10 | 37.9 ± 30 |

It is evident from the above results for the new formation of glucose and glycogen that compounds I and II still do not have any significant effect at 3 mg/kg whereas prednicarbate is already exhibiting a small but significant (p 0.05, t test) effect at this concentration. The therapeutic advantage (low systemic effect) is therefore greater in the case of the compounds I and II than it is in the case of prednicarbate.

EXAMPLES

The following general comments should be made with regard to the examples given below:

The melting points are measured in a Tottoli apparatus (from Büchi) or on a type 7841 Kofler hot bench from Reichert (Austria), and are not corrected. The IR spectra (in KBr) are plotted using a Perkin Elmer 521 grating spectrophotometer. Only the characteristic bands are cited in each case. The UV spectra were plotted (in methanol) using a Beckmann DK 1 A spectrophotometer. The mass spectroscopic investigations (MS) are mainly carried out using an MS 9 apparatus (from AEI). The MS spectra (molecular weight peak) are chiefly given in: MS=m/z=... (M+H$^+$) (measurement using pure isotopes), i.e. the monoisotopic molar mass was registered in each case. FAB MS spectra were measured as a rule. Silica gel $F_{254}$ ready-to-use plates (from Merck) were employed for the thin layer chromatography (TLC). Unless otherwise indicated, methylene chloride: methanol =19:1 was used as the eluent (elution distance 7 cm). Development was carried out twice in each case. The spots were either detected at 254 nm using a UV lamp or else rendered visible either by spraying with 10% methanolic sulfuric acid or by heating at 100° C. The $R_F$ values are in every case only relative. 15 silica gel 60, particle size 0.063–0.2 mm (from Merck), was employed for the column chromatography.

When carbonyl chlorides are used in the reactions, absolute dioxane is often advantageously added to the reaction mixture, for example in the case of benzoyl chloride where the ratio of dioxane/pyridine is about 1:1, and, in order to accelerate the reaction, the reaction mixture is often, particularly in the case of sterically hindered or less reactive carbonyl chlorides or carboxylic anhydrides, heated at about 60° C. (monitoring of the course of the reactions using TLC).

The reaction products can be characterized by thin layer chromatography (TLC); in this context, the reaction products have $R_F$ values of about 0.65–0.75. As a rule, the reaction products are characterized by mass spectra using MS=m/z=... (M+H$^+$) (FAB spectra as a rule); the monoisotopic molar mass is registered in each case. The M+H$^+$ values were rounded up in each case. IR, $^1$H-NMR and UV spectra can also be enlisted for the characterization.

Example 1

Prednisolone 17-ethyl carbonate 21-benzoate a) 0.23 ml of benzoyl chloride are added dropwise, at 0° C. and while stirring, to a solution of 0.65 g (0.0015 mol) of prednisolone 17-ethyl carbonate in 5 ml of absolute acetone and 2 ml of absolute pyridine. The mixture is stirred at room temperature (21° C.) for 20 h., is then warmed, if starting material can still be detected by thin layer chromatography, for a few more hours (about 5 h.) at 40°–50° C. is allowed to cool and is then poured into 60 ml of a half-saturated aqueous solution of sodium chloride; the aqueous phase is then decanted off from the oil or wax which has precipitated out (if crystals precipitate, these are filtered off), and the precipitate is taken up in methylene chloride, after which the organic phase is washed with water and dried, e.g. with sodium sulfate, and the solvent is distilled off. The remaining residue (0.8 g) is dissolved in ethanol and methylene chloride and subsequently recrystallized by adding diethyl ether or diisopropyl ether, and yields 0.58 g of prednisolone 17-ethyl carbonate 21-benzoate with a m.p. of 133°–135° (decomp.).

In TLC (eluent: $CH_2Cl_2$:$CH_3OH$=19:1), this material, like the abovementioned precipitate, still exhibits subsidiary spots, mainly at $R_F$ values of about 0.5–0.55 and about 0.9, in addition to the main spot at $R_F$=0.7. In order to purify it (TLC), it is subjected to fractional chromatography (50 ml fractions) on silica gel [particle size 0.063–0.2000 mm (Merck AG), column, 20×3 cm] using methylene chloride/ methanol=998:2. The fractions which subsequently show an $R_F$ value of about 0.7 in the TLC are combined. After distilling off the eluent, 2.4 g (3.8 g in the best repeat batch) of crystallized prednisolone 17-ethyl carbonate 21-benzoate with a m.p. of 136° C. are obtained from diethyl ether and/or ethanol, methylene chloride and diethyl ether (or diisopropyl ether).

MS: m/z=537–(M+H⁺)
TLC: $R_F$=0.7 (SM=0.4)
(SM=starting material)
The abovementioned oily or waxy/oily precipitate also has a value after drying of: MS:m/z=537 (M+H⁺)

b) 0.45 ml of benzoylchloride in 10 ml of absolute dioxane are added dropwise, at 0° C. and while stirring, to a solution of 1.3 g of prednisolone 17-ethyl carbonate in 12 ml of pyridine, and the mixture is then stirred at 21° C. for 48 h. (and if necessary stirred at 40°–60° C. for a further 4–6 h. until SM can no longer be detected by TLC). After analogous working up, isolation and, where appropriate, purification, as given under Example 1 a), 1.1 g of prednisolone 17-ethyl carbonate 21-benzoate are obtained, after crystallization from diethyl ether, which, with regard to m.p., MS and TLC, is identical with the reaction product according to Example 1 a). If the above reaction mixture is stirred at 0°–5° C., longer reaction times are often required than those given above.

c) If 0.6 ml of benzoic anhydride are employed in Example 1 b) instead of benzoylchloride, and the reaction and the working up and purification are carried out in the same manner as described under Examples 1 b) and 1 a), the same reaction product, having the same parameters, is obtained as described under Examples 1 b) and 1 a).

Example 2

Prednisolone 17-ethyl carbonate 21-phenylacetate
a) 0.65 g of prednisolone 17-ethyl carbonate are reacted, worked up and purified chromatographically in the same manner as indicated under Example 1 a). However, 0.23 g of phenylacetyl chloride are used instead of the benzoyl chloride employed in that previous example. Following recrystallization from tert-butanol/diisopropyl ether, 0.44 g of prednisolone 17-alkyl carbonate 21-phenylacetate are obtained with a m.p. of about 180° C. In addition to the main spot at $R_F$=0.8, several subsidiary spots, which are for the most part weak, are detected below and above $R_F$=0.8.
MS: m/z=551 (M+H⁺)
TLC: $R_F$=0.80 ($R_F$(SM)=0.45)

b) A freshly prepared mixture of 26 mg of concentrated sulfuric acid in 2.5 ml of absolute pyridine (suspension of pyridinium sulfate) is added, at 20° C. and while stirring, to a solution of 1.1 g (0.0025 mol) of prednisolone 17-ethyl carbonate and 1.2 g (0.0088 mol) of phenylacetic acid (dried at about 50°–60° C. in vacuo over $P_2O_5$ for 5 h.) in 6 ml of absolute pyridine. After stirring for 15 min., 720 mg (0.0035 mol) of N,N'-dicyclohexylcarbodiimide are added. A crystalline precipitate of the N,N'-dicyclohexylurea which has been formed soon appears in the initially clear solution. Stirring is continued until TLC no longer detects starting material and detects the reaction product at $R_F$=0.8 (as a rule, a reaction period of 16 hours; a longer reaction period, e.g. standing or stirring over the weekend, does not impair the reaction result). After this, 0.3 ml of acetic acid are added and the mixture is left to stand for a further 1 h. at 20° C. and then 24–48 h. in a deep-freeze (about −15° C.). The precipitated N,N'-dicyclohexylurea is filtered off and washed with cold pyridine (about −15° C.), and the filtrate is stirred into about 400 ml of a quarter-saturated aqueous solution of sodium chloride; about 5 ml of ethanol are added and the oily-crystalline precipitate is filtered off, washed several times with water and then taken up in about 20 ml of methylene chloride. After drying with sodium sulfate, the solvent is distilled off and the residue is crystallized by adding diethyl ether or diisopropyl ether. 1.1 g of prednisolone 17-ethyl carbonate 21-phenylacetate with a melting point of 179°–183° C. are obtained and can be recrystallized from tertbutanol/diethylether.

M.P.: 184°–185° C.
MS: m/z=551 (M+H⁺)
TLC: $R_F$=0.80 ($R_F$ of SM=0.45)
A chromatographic purification, as given under Example a), is not required for preparation in pure condition in this instance.

c) A further mixture is made up which is analogous to that described under Example 2 b); however, the acidic catalyst, concentrated sulfuric acid in pyridine, is omitted. A TLC sample fails to indicate any further starting material after a reaction period which is about 5 times longer than that given under Example 2 b). After working up and purification which are analogous to those described under Example 2 b), 0.9 g of prednisolone 17-ethyl carbonate 21-phenylacetate are obtained having the same parameters as those given under Example 2 b).
The title compound, likewise having the same parameters, is also obtained if absolute dimethylformamide is used as the solvent instead of pyridine.

d) A further mixture is prepared which is analogous to that described under Example 2 b). However, 60 mg of p-toluenesulfonic acid are added instead of the sulfuric acid. After working up and purification which are analogous to those given under Example 2 b ), 1.2 g of prednisolone 17-ethyl carbonate 21-phenylacetate are obtained having the same parameters as given in Example 2 b).

Example 3

Prednisolone 17-ethyl carbonate 21-(3)-phenylpropionate
4.15 g of 3-phenylpropionyl chloride are added dropwise, at 0° C. and while stirring, to a solution of 10 g of prednisolone 17-ethyl carbonate in 84 ml of absolute acetone and 32 ml of absolute pyridine, and the mixture is stirred under reflux for 6 hours. A TLC sample still fails to show complete reaction. For this reason, a further 2.5 g of 3-phenylpropionyl chloride and 30 ml of pyridine are added dropwise, and the mixture is stirred under reflux for a further 6 h. (TLC sample shows complete reaction). The mixture is stirred into 1 l of water containing sodiumchloride and the oil which has precipitated is then taken up in ethyl acetate, washed with water and dried, and the solvent is then distilled off. For the purification, column chromatography (eluent ethyl acetate) is carried out on 200 g of silica gel (particle size 70–200 μm). The fractions which are uniform by TLC are combined, the eluent is distilled off, and the residue is crystallized from diethylether. 9.0 g of the abovementioned title compound are obtained.
M.p.: 146°–147° C.
MS: m/z=565 (M+H⁺)
TLC: $R_F$=0.7

Example 4

Prednisolone 17-ethyl carbonate 21-phenoxyacetate
10 g of prednisolone 17-ethyl carbonate are reacted, worked up and purified chromatographically in the same way as described in Example 3. However, a total of 8.4 g of phenoxyacetyl chloride is employed in each case instead of the 3-phenylpropionyl chloride. 6.8 g of the abovementioned title compound with an m.p. of 128° C. are obtained from diethyl ether.
MS: m/z=567 (M+H⁺)
TLC: $R_F$=0.7

Example 5

Prednisolone 17-ethyl carbonate 21-cinnamic ester
0.21 g of cinnamoyl chloride are added dropwise, at 0° C. and while stirring, to a solution of 0.6 g of prednisolone 17-ethyl carbonate in 5 ml of absolute acetone and 1.9 ml of absolute pyridine. The mixture is left to stir at 20° C. for 6 to 24 h (until TLC no longer detects any starting material), and is then poured into 100 ml of water (half-saturated with NaCl); the precipitate is collected by decantation or filtering and dissolved in (acid-free) methylene chloride, washed with water and dried with $Na_2SO_4$; the solvent is then distilled off and the residue is chromatographed, using $CH_2Cl_2/CH_3OH=950:50$ as the eluent, on silica gel (70–200 mm particle size) in 100 ml fractions (column: 27×3 cm). 390 mg of the abovementioned title compound can be isolated from fractions 30–40 (depending on the TLC result) by crystallizing from diisopropyl ether or diethyl ether.
M.p.: 138° C.
MS: m/z=563 (M+H$^+$)
TLC: $R_F$=0.7

Example 6

Prednisolone 17-ethyl carbonate 21-(p-anisic) ester

In the same manner as described in Example 5, 0.6 g of prednisolone 17-ethyl carbonate are reacted with 0.21 g of p-anisoyl chloride instead of the cinnamoyl chloride; working up is carried out, and the product is prepared in pure form by column chromatography. 540 mg of the abovementioned title compound are obtained from diethylether.
M.p. 194° C.
MS: m/z=567 (M+H$^+$)
TLC: $R_7$=0.7

Example 7

Prednisolone 17-ethyl carbonate 21-(thienyl-2-acetic) ester

In the same manner as described in Example 5, 0.6 g of prednisolone 17-ethyl carbonate are reacted with 0.21 g of 2-thienylacetyl chloride instead of the cinnamoyl chloride, and then worked up and prepared in pure form by column chromatography. 340 mg of the abovementioned title compound are obtained from diethyl ether. M.p. 195°–198° C.
MS: m/z=557 (M+H$^+$)
TLC: $R_F$=0.7

Example 8

Prednisolone 17-ethyl carbonate 21-(thiophene-2-carboxylic) ester

In the same manner as described in Example 5, 0.6 g of prednisolone 17-ethyl carbonate are reacted with 0.21 g of thiophene-2-carbonyl chloride instead of the cinammoyl chloride; working up then takes place and the product is prepared in pure form by column chromatography. 440 mg of the abovementioned title compound are obtained from diethyl ether. M.p.142° C.
MS: m/z=543(M+H$^+$);
TLC: $R_F$=0.7

Example 9

Prednisolone 17-ethyl carbonate 21-[3-(2-thienyl)acrylic] ester

In the same manner as described in Example 5, 0.6 g of prednisolone 17-ethyl carbonate are reacted with 0.21 g of thienylacryloyl chloride instead of the cinnamoyl chloride; working up then takes place and the product is prepared in pure form by column chromatography. 560 mg of the abovementioned title compound are obtained from diethyl ether. M.p. 177° C.
MS: m/z=569 (M+H$^+$); TLC: $R_F$=0.7

Example 10

Prednisolone 17-ethyl carbonate 21-(furan-2-carboxylic) ester

In the same manner as described in Example 5, 0.6 g of prednisolone 17-ethyl carbonate are reacted with 0.21 g of furan-2-carbonyl chloride instead of the cinnamoyl chloride; working up then takes place and the product is prepared in pure form by column chromatography. 540 mg of the abovementioned title compound are obtained from diethyl ether. M.p. 170° C. (in another batch, the Fp was =214° C., double melting point)
MS: m/z=527 (M+H$^+$)
TLC: $R_F$=0.7

Example 11

Prednisolone 17-ethyl carbonate 21-[3-(2-furylacrylic)] ester

In the same manner as described in Example 5, 0.6 g of prednisolone 17-ethyl carbonate are reacted with 0.21 g of β- or 3-(2-furyl)acryloyl chloride instead of the cinnamoyl chloride; working up then takes place and the product is prepared in pure form by column chromatography. 650 mg of the abovementioned title compound are obtained from diethyl ether. M.p. 149° C. or 199° C. (double melting point?)
MS: m/z=553 (M+H$^+$)
TLC: $R_F$=0.7

Example 12

Prednisolone 17-ethyl carbonate 21-phenylacetate 408 mg (0.003 mol) of anhydrous phenylacetic acid and 492 mg (0.003 mol) of N,N'-carbonyldi(1H-1,2,4-triazole) or an equimolar quantity of N,N'-carbonyldiimidazole are stirred at 20° C. in 15 ml of absolute pyridine for 1 h. After that, 1.43 g (0.0033 mol) of dried prednisolone 17-ethyl carbonate in 10 ml of absolute pyridine are added dropwise. After adding a catalytic quantity (5 mg) of sodium hydride, the mixture is stirred at 20° C. over the weekend, and then left to stand at 20° C. overnight. After filtering off a precipitate which has formed, the filtrate is stirred into 200 ml of water (containing sodium chloride)+10 ml of ethanol. By means of decanting, the oily precipitate which has separated out is dissolved in methylene chloride and fractionated chromatographically on silica gel in analogy with Example 1 a). The crystals obtained from tert-butanol/diethyl ether show the same parameters as the reaction product according to Example 2 a) and therefore represent prednisolone 17-ethyl carbonate 21-phenyl acetate.

Example 13

Prednisolone 17-n-propyl carbonate 21-(3)-phenylpropionate

A solution of 300 mg of 3-phenylpropionyl chloride in 1 mg of absolute dioxane is added dropwise, at 0° C. and while stirring, to a solution of 340 mg of prednisolone 17-n-propyl carbonate in 3 mg of absolute pyridine. After being stirred at 0° C. for 5 to 6 h. (TLC indicates completed formation of the desired reaction product), the mixture is poured into a 100 ml half-saturated aqueous solution of sodium chloride, and the precipitate (oily or wax) is isolated by way of a fluted filter; this precipitate is then taken up with methylene chloride (or ethyl acetate), which is washed with water and dried with sodium sulfate, and the solvent is then distilled off in vacuo. The residue is then crystallized using diisopropyl ether or diethyl ether or petroleum ether, then filtered off and, where appropriate recrystallized from ethanol/ether (optionally with the addition of petroleum ether). 405 mg of the abovementioned title compound are obtained with a m.p. of: 128°–134° C.

MS: m/z=579 (M+H$^+$)
TLC: R$_f$≈0.7

Example 14

Prednisolone 17-isopropyl carbonate 21-phenoxyacetate

In the same manner as described under Example 13, 340 mg of prednisolone 17-isopropyl carbonate are reacted with 300 mg of phenoxyacetyl chloride instead of the 3-phenylpropionyl chloride, and then worked up; the title compound is then prepared in pure crystalline form. 390 mg of the abovementioned title compound are obtained; (amorph.).

MS: m/z=581 (M+H$^+$)
TLC: R$_f$≈0.7

Example 15

Prednisolone 17-n-butyl carbonate 21-cinnamic ester

In the same manner as described under Example 13, 350 mg of prednisolone 17-n-butyl carbonate are reacted with 320 mg of cinnamoyl chloride instead of the 3-phenylpropionyl chloride; working up then takes place and the product is prepared in pure crystalline form. 410 mg of the abovementioned title compound are obtained.

M.p. 115°–120° C.
MS: m/z=591 (M+H$^+$)
TLC: R$_f$≈0.7

Example 16

Prednisolone 17-n-valeryl carbonate 21-cinnamic ester

If, in Example 15, 360 mg of prednisolone 17-n-valeryl carbonate, instead of the corticoid mentioned in that example, are reacted with cinnamoyl chloride, 390 mg of the abovementioned title compound are then obtained in amorphous form.

MS: m/z=605 (M+H$^+$)
TLC: R$_f$≈0.75

Example 17

Prednisolone 17-methoxyethyl carbonate 21-cinnamic ester

If, in Example 15, 350 mg of prednisolone 17-methoxyethyl carbonate, instead of the corticoid mentioned in that example, are reacted with cinnamoyl chloride, 400 mg of the abovementioned title compound are then obtained, after working up and crystallization from diethyl ether, as a wax.

MS: m/z=593 (M+H$^+$)
TLC: R$_f$≈0.7

Example 18

Prednisolone 17-n-propyl carbonate 21-phenylacetate

If, as described in Example 2 b), 1.1 g of prednisolone 17-n-propyl carbonate are reacted with 1.2 g of phenylacetic acid and 720 mg of N,N'-dicyclohexylcarbodiimide as well as pyridinium sulfate, 1.0 g of the abovementioned title compound is then obtained (m.p.: 178° C.).

MS: m/z=565 (M+H$^+$)
TLC: R$_f$≈0.8

Example 19

Prednisolone 17-isopropyl carbonate 21-phenylacetate

If, instead of the corticoid mentioned in Example 18, 1.1 g of prednisolone 17-isopropyl carbonate are reacted with phenylacetic acid, 1.1 g of the abovementioned title compound are then obtained. M.p.=200°–202° C.

MS: m/z=565 (M+H$^+$)
TLC: R$_f$≈0.8

Example 20

Prednisolone 17-n-butyl carbonate 21-phenylacetate

If, instead of the corticoid mentioned in Example 18, 1.15 g of prednisolone 17-n-butyl carbonate are reacted with phenylacetic acid, 1.2 g of the abovementioned title compound are then obtained. M.p.: 198° C.

MS: m/z=579 (M+H$^+$) TLC: R$_f$≈0.8

Example 21

Prednisolone 17-tert-butylmethyl carbonate 21-p-methylphenylacetate

If, instead of the corticoid mentioned in Example 18, 1.2 g of prednisolone 17-tert-butylmethyl carbonate are reacted with 1.3 g of p-methylphenylacetic acid, 1.1 g of the abovementioned title compound are then obtained; (amorph.).

TLC: R$_f$≈0.85

Example 22

Betamethasone 17-ethyl carbonate 21- (3) -phenylpropionate

In the same manner as described under Example 13, 340 g of betamethasone 17-ethyl carbonate are reacted with 300 mg of 3-phenylpropionyl chloride. 380 mg of the abovementioned title compound are obtained with a m.p. of ~167° C.

MS: m/z=597 (M+H$^+$)
TLC: R$_f$≈0.8

Example 23

Betamethasone 17-ethyl carbonate 21-phenoxyacetate

In the same manner as described under Example 13, 340 mg of betamethasone 17-ethyl carbonate are reacted with 300 mg of phenoxyacetyl chloride instead of the 3-phenylpropionyl chloride. 380 mg of the abovementioned title compound are obtained with a m.p. of 185° C.

MS: m/z=599 (M+H$^+$)
TLC: R$_f$≈0.75

Example 24

Betamethasone 17-ethyl carbonate 21-cinnamic ester

In the same manner as described under Example 13, 340 mg of betamethasone 17-ethyl carbonate are reacted with 320 mg of cinnamoyl chloride instead of the acid chloride mentioned in that example. 310 mg of the abovementioned title compound are obtained; m.p.: 178° C.

MS: m/z=595 (M+H$^+$)
TLC: R$_f$≈0.7

Example 25

Betamethasone 17-ethyl carbonate 21-phenyl acetate a.) In the same manner as described under Example 13, 340 mg of betamethasone 17-ethyl carbonate are reacted with 300 mg of phenylacetyl chloride instead of the 3-phenylpropionyl chloride. 230 mg of the abovementioned title compound are obtained with a m.p. of 168° C.

MS: m/z=583 (M+H$^+$)
TLC: R$_F$≈0.7 b.) If, as described in Example 2 b), 1.1 g of betamethasone 17-ethyl carbonate are reacted with 1.2 g of phenylacetic acid and 720 mg of N,N'-dicyclohexylcarbodiimide as well as pyridinium sulfate, and then worked up, 1.1 g of the abovementioned title compound having the same physical and spectral parameters as indicated under Example 25 a) are then obtained.

Example 26

Betamethasone 17-ethyl carbonate 21-(thienyl-2-acetic) ester

In the same manner as described in Example 5, 0.3 g of betamethasone 17-ethyl carbonate are reacted with 0.21 g of 2-thienylacetyl chloride instead of the cinnamoyl chloride, and then worked up. 400 mg of the abovementioned title compound are obtained from diethyl ether.
M.p. 153°–159° C. (indistinct)
MS: m/z=589 (M+H$^+$)
TLC: R$_F$=0.7

Example 27

Betamethasone 17-ethyl carbonate 21-(furan-2-carboxylic) ester

In the same manner as described in Example 5, 0.3 g of betamethasone 17-ethyl carbonate are reacted with 0.21 g of furan-2-carbonyl chloride instead of the cinnamoyl chloride, and then worked up. 540 mg of the abovementioned title compound are obtained from diethyl ether.
M.p.≈170° C. (indistinct)
MS: m/z=559 (M+H$^+$)
TLC: R$_F$=0.7

Example 28

Betamethasone 17-ethyl carbonate 21-(indole-3-acetic) ester

In the same manner as described in Example 29), 1.1 g of betamethasone 17-ethyl carbonate are reacted with 1.2 g of indolyl-3-acetic acid and 720 mg of N,N'-dicyclohexylcarbodiimide as well as pyridinium sulfate, and then worked up. 0.95 g of the abovementioned title compound are obtained as a wax, which was not purified by chromatography.
MS: m/z=622 (M+H$^+$)
TLC: R$_F$=0.65 (Ms major spot)

Example 29

Prednisolone 17-ethyl carbonate 21-(indole-3-acetic) ester

Pyridinium sulfate (comprising 56 mg of conc. sulfuric acid in 2.5 ml of absolute pyridine, in accordance with Example 2 b) is added, at 20° and while stirring, to a solution of 2.2 g of prednisolone 17-ethyl carbonate and 3.1 g of 3-indoleacetic acid (dried) in 15 ml of absolute pyridine. After stirring (20° C.) for 30 minutes, 1.55 g of N,N'-dicyclohexylcarbodiimide are added. After stirring at 20° C. for 48 hours, the mass spectrum shows an m/z=590.4 (M+H$^+$) and no m/z=433 (M+H$^+$) for the precursor steroid. Following further treatment and working up in analogy with Example 2 b), and after pouring into about 500 ml of half-saturated sodium chloride solution, an oily precipitate is obtained which changes into a wax. The wax is decanted or filtered off, washed with water and then dried in a desiccator in vacuo over P$_2$O$_5$. After grinding with petroleum ether, 1.55 g of the title compound are obtained as an amorphous product. MS (of wax or of amorphous material): m/z=590 (M+H$^+$) TLC≈0.75 (major spot=Ms+a few weak subsidiary spots). For purification, chromatography is carried out using methylene chloride/methanol=99.5:0.5 on silica gel (column: diameter=5 cm; h=20 cm). The resultant eluate fractions having R$_F$≈0.75 are combined and freed from the solvents by distillation. The residue is crystallized from diethyl ether. 1.2 g of the title compound with a m.p. of 145° C. are obtained having the same parameters for MS and TLC as the waxy or amorphous title compound.

Example 30

Dexamethasone 17-ethyl carbonate 21-phenylacetate a) If, as described in Example 29), 0.55 g of dexamethasone 17-ethyl carbonate are reacted at room temperature with 0.6 g of phenylacetic acid, instead of the 3-indolylacetic acid, and with 360 mg of N,N'-dicyclohexylcarbodiimide as well as 15 mg of concentrated sulfuric acid in 1.25 ml of pyridine (=pyridinium sulfate) in a total of 4.5 ml of absolute pyridine, worked up, isolated as a wax or in the amorphous state, and (where appropriate) prepared in pure crystalline form by chromatography, 540 mg of dexamethasone 17-ethyl carbonate 21-phenyl acetate are then obtained with a m.p.: 185°–189° C.
MS: m/z=583 (M+H$^+$) (crystallized, as a wax or
TLC: R$_F$≈0.7 in amorphous form)

In the same manner as described in Example 30 a), the following are obtained, starting (instead of from dexamethasone 17-ethyl carbonate)

b) from hydrocortisone 17-ethyl carbonate, hydrocortisone 17-ethyl carbonate 21-phenylacetate (MS: m/z=553 (M+H$^+$); TLC: R$_F$≈0.8)

c) from cortisone 17-ethyl carbonate, cortisone 17-ethyl carbonate 21-phenylacetate (R$_F$≈0.8)

d) from 6α-methylprednisolone 17-ethyl carbonate, 6α-methylprednisolone 17-ethyl carbonate 21-phenylacetate (R$_F$≈0.75)
(MS: m/z=565 (M+H$^+$))

e) from prednisone 17-ethyl carbonate, prednisone 17-ethyl carbonate 21-phenylacetate (R$_F$≈0.7)

f) from 6α-fluoroprednisolone 17-ethyl carbonate, 6α-fluoroprednisolone 17-ethyl carbonate 21-phenylacetate (R$_F$≈0.8)
(MS: m/z=569 (M+H$^+$))

g) from 6α-fluorodexamethasone 17-ethyl carbonate, 6α-fluorodexamethasone 17-ethyl carbonate 21-phenylacetate (R$_F$≈0.8; MS: m/z 601 (M+H$^+$))

h) from 6α-fluorobetamethasone 17-ethyl carbonate, 6α-fluorobetamethasone 17-ethyl carbonate 21-phenylacetate (R$_F$≈0.75)

i) from 6α, 16α-dimethylprednisolone 17-ethyl carbonate, 6α, 16α-dimethylprednisolone 17-ethyl carbonate 21-phenylacetate (R$_F$≈0.75)

j) from the 17α-ethyl carbonate of "Reichstein's substance S", the 17α-ethyl carbonate, 21-phenylacetate of "Reichstein's substance S" (R$_F$≈0.85; MS: m/z=537 (M+H$^+$))

k) from beclomethasone 17α-ethyl carbonate, beclomethasone 17α-ethyl carbonate 21-phenylacetate (R$_F$≈0.8) l) from 6α-methyl-9α-fluoroprednisolone 17-ethyl carbonate, 6α-methyl-9α-fluoroprednisolone 17-ethyl carbonate 21-phenylacetate (R$_F$≈0.85; MS: m/z=583 (M+H$^+$))

m) from betamethasone 17-n-propyl carbonate, betamethasone 17-n-propyl carbonate 21-phenylacetate (R$_F$≈0.8)

n) from dexamethasone 17-isopropyl carbonate, dexamethasone 17-isopropyl carbonate 21-phenylacetate (R$_F$≈0.75)

o) from prednisolone 17-n-propyl carbonate, prednisolone 17-n-propyl carbonate 21-phenylacetate ($R_F \approx 0.8$)

p) from prednisolone 17-isopropyl carbonate, prednisolone 17-isopropyl carbonate 21-phenylacetate ($R_F \approx 0.8$)

q) from prednisolone 17-n-butyl carbonate, prednisolone 17-n-butyl carbonate 21-phenylacetate ($R_F \approx 0.8$)

r) from prednisolone 17-isobutyl carbonate, prednisolone 17-isobutyl carbonate 21-phenylacetate ($R_F \approx 0.7$)

s) from prednisolone 17-methoxyethyl carbonate, prednisolone 17-methoxyethyl carbonate 21-phenylacetate ($R_F \approx 0.8$)

as an oil or wax or in the amorphous form or crystallized.

Example 31

Betamethasone 17-ethyl carbonate 21-phenylacetate a) 120 mg of 4-dimethylaminopyridine and 1.75 g of dicyclohexylcarbodiimide are added, at 0° C. and while stirring, to a solution of 2.10 g of prednisolone 17-ethyl carbonate and 1.20 g of phenylacetic acid in 40 ml of absolute methylene chloride. The reaction solution, which is initially clear, soon becomes turbid. After stirring at room temperature for about 36 hours, a TLC sample is no longer able to detect starting material. The mixture is then stored at −15° C. (deep freeze) for 2 days and the dicyclohexylurea which has precipitated out is then filtered off and washed with a little cold (−15° C.) methylene chloride; the organic solvent is subsequently stripped off in vacuo. The remaining residue is crystallized from boiling diethyl ether and crystallized from ethanol/diethyl ether. 1.9 g of the abovementioned title compound (radiantly white crystals) are obtained having the same parameters (MS, TLC and melting point) as given under Example 20 b). The melting point is about 2° higher than that in Example 2 b): m.p. 166°–168° C.

b) the methylene chloride is replaced as solvent by dimethylformamide in a mixture which is analogous to Example 31a. In other respects, the procedure is precisely the same as that given under Example 30a). After working up, 1.7 g of the abovementioned title compound are obtained with an m.p.: 165°–167° C.

Example 32

Prednisolone 17-ethyl carbonate 21-phenylacetate a) A mixture of 216 mg of prednisolone 17-ethyl carbonate or 270 mg of 21-(tert.-butyldimethylsiloxy)prednisolone 17-ethyl carbonate, 136 mg of phenylacetic acid, 210 mg of trifluoroacetic anhydride and 6 mg of anhydrous p-toluenesulfonic acid is boiled under reflux for 7 hours in 40 ml of absolute toluene or benzene. After this, the mixture is poured into 6% aqueous sodium bicarbonate solution and thoroughly stirred. Washing with water then takes place, followed by drying; the solvent is then stripped off and chromatography takes place on silica gel (see example 2b). The product running at TLC=$R_F \approx 0.7$ is crystallized from diethyl ether. It is identical in all parameters to the reaction product given under Example 2.

b) In a further mixture, 1.5 g of phenylacetic acid and 0.75 ml of trifluoroacetic anhydride are added to 700 mg of prednisolone 17-ethyl carbonate in 20 ml of absolute dioxane. After being stirred at 20° C. for 30 hours, the mixture was stirred into 40 ml of water containing 2 g of sodium bicarbonate. After having been dried, the resultant waxy product is chromatographed as described under Examples 32a) or 2b), and then crystallized from diethyl ether. The abovementioned title compound is obtained having the same parameters as those given under Example 2.

Example 33

Prednisolone 17-ethyl carbonate 21-[4-(4-(N,N)-(bis(2-chloroethyl)amino)phenyl)butyrate]

Pyridinium sulfate (comprising 110 mg of conc. sulfuric acid in 2.5 ml of absolute pyridine, prepared in accordance with Example 2b) is added, at 20° C. and while stirring, to a solution of 4.32 g of prednisolone 17-ethyl carbonate and 3.5 g of 4-(4-(N,N)-(bis(2-chloroethyl)amino)phenyl)butyric acid (=chlorambucil) in 30 ml of absolute pyridine. After the mixture has been stirred at 20° C. for 20 minutes, 3 g of N,N'-dicyclohexylcarbodiimide are added. The mixture is then stirred at 20° C. for 48 hours, after which 100 mg of ethyl acetate and 100 ml of water+ice are added. The pH is adjusted to about 2.5 to 3.0 with 5N hydrochloric acid (aqu.), and the organic phase is then washed successively with water, sodium carbonate solution (aqu.) and water. Isolation takes place after drying ($Na_2SO_4$), and the residue is digested with petroleum ether. Filtration takes place and the amorphous to waxy reaction product is dried in vacuo over $P_2O_5$. 5.8 g of the abovementioned title compound are obtained, exhibiting a main spot at $R_{F \approx 0.8}$ in TLC.

Example 33 b

Optimization of the process which was originally given in Example 33 (=33a)): Prednisolone 17-ethyl carbonate 21-[4-(4-(N,N)-(bis(2-chloroethyl)amino)phenyl)butyrate] (crystallized product)

Pyridinium sulfate (comprising 300 mg of conc. sulfuric acid in 10 ml of absol. pyridine, prepared in accordance with Example 2b) is added, at 20° C. and while stirring, to a solution of 8.64 g of prednisolone 17-ethyl carbonate and 7.2 g of 4-(4-(N,N)-(bis(2-chloroethyl)amino)phenyl)butyric acid (=chlorambucil) in 50 ml of absol. pyridine. After the mixture has been stirred at 20° C. for 20 minutes, 5.77 g of N,N-dicyclohexylcarbodiimide are added. After this mixture has been stirred at 20° C. for 48 hours, 2 ml of glacial acetic acid are added and the mixture is left for 48 hours in a deep freeze (−15° C.). The N,N'-dicyclohexylurea (6.1 g) which has precipitated out is filtered off and approximately 300 ml of a half-saturated aqueous solution of sodium chloride is added to the filtrate, whereupon an oil precipitates out. The oil is filtered off using a fluted filter and is treated with 400 ml of water, as a result of which it changes into a wax within the space of 48 hours. The wax is filtered off, washed with water and dried, the last occasion being in a vacuum desiccator. It is dissolved in boiling isopropanol under reflux and this solution is allowed to cool to 20° C., whereupon a thick crop of crystals soon precipates out. These crystals are filtered off and washed with isopropanol which is cooled to 0° C. After drying, 7.1 g of the abovementioned title compound are obtained in crystalline form. M.p. from 110° to 112° C.

MS: m/z=718

TLC: $R_F \cong 0.8$

The $H^1$-NMR spectrum was recorded in D-DMSO and conforms to the given nomenclature notation.

Example 34

Prednisolone 17-ethyl carbonate 21-phenylacetate 435 mg of N,N'-dicyclohexylcarbodiimide, 43 mg of N,N'-dimethylaminopyridine and 700 mg of prednisolone 17-ethyl carbonate are added successively, at 0° C. and while stirring, to a solution of 286 mg of phenylacetic acid in 14 ml of absolute methylene chloride. After the mixture has been stirred at 20° C. for 18 hours, washing takes place with 40 ml of saturated aqueous solution of sodium hydrogen carbonate, with 30 ml of aqueous hydrochloric acid (2 mol dm$^{-3}$) and with water. The methylene chloride phase is evaporated in vacuo in a rotary evaporator and the residue is crystallized from ethanol/methylene chloride/diethyl ether. 520 mg are obtained of the abovementioned title compound, which is identical in all its parameters with the product obtained in accordance with Examples 2a or b.

Example 35

Prednisolone 17-ethyl carbonate 21-phenylacetate 150 mg of phenylacetic acid and 432 mg of prednisolone 17-ethyl carbonate are dissolved in 3 ml of abs. methylene chloride and 5 ml of abs. pyridine, and 0.25 ml of a 50% solution of propanephosphonic anhydride in abs. methylene chloride and 10 mg of 4-dimethylaminopyridine are then added. After having been stirred at about 40° C. (oil bath) for 8 hours, the mixture is poured into ice water, which contains sodium bicarbonate for neutralization. Extraction then takes place with ethyl acetate, followed by washing with aqueous KHSO$_4$ solution and water. After the distillation, the residue is chromatographed in analogy with Example 1a). In addition to starting material and prednisolone, one eluate fraction also contains the desired abovementioned title compound having the same parameters as given under Example 2b.

Example 36

Prednisolone 17-ethyl carbonate 21-phenylacetate

A solution of 400 ml of phenylacetic anhydride in 1 ml of absolute dioxane is added dropwise, at 0° C. and while stirring, to a solution of 226 mg of prednisolone 17-ethyl carbonate in 2 ml of absolute pyridine. After having been stirred at 0° C. for 5 to 6 hours and at 20° C. for 16 hours, the mixture is poured into 100 ml of a half-saturated aqueous solution of sodium chloride, and the waxy precipitate is then isolated by way of a fluted filter and taken up with methylene chloride (or ethyl acetate); washing with water and drying with sodium sulfate then follows, after which the solvent is distilled off in vacuo. The residue is crystallized with diisopropyl ether or diethyl ether or petroleum ether, and then filtered off and recrystallized from ethanol/ether (optionally with the addition of petroleum ether). 145 mg of the abovementioned title compound are obtained with a m.p.: 183° C.
MS: m/z=551(M+H$^+$)
TLC: R$_F$≈0.7

Example 37

Prednisolone 17-ethyl carbonate 21-[3,4-methylenedioxy-benzoic] ester

In the same manner as described under Example 36, 220 mg of prednisolone 17-ethyl carbonate are reacted with 280 mg of 3,4-(methylenedioxy)benzoyl chloride or 600 mg of 3,4-methylenedioxybenzoic anhydride instead of the phenylacetic anhydride, and then worked up. 180 mg of the abovementioned title compound are obtained as a wax (from petroleum ether).
MS: m/z=581(M+H$^+$)
TLC: R$_F$≈0.7

Example 38

Prednisolone 1-ethyl carbonate 21-phenylcarbonate

A solution of 4 ml of phenyl chloroformate in 12 ml of absolute dioxane is added dropwise, at 0° C. and while stirring, to a solution of 2.26 g of prednisolone 17-ethyl carbonate in 9 ml of absolute pyridine, resulting in the appearance of an oily precipitate. After having been stirred at 0° C. for 7 hours, the mixture is poured into 200 ml of half-saturated sodium chloride solution (aq), and the precipitated oil is filtered off by way of a fluted filter and taken up with methylene chloride; the residue is chromatographed on silica gel (35–70 µm) using methylene chloride/methanol=99.5:0.5. The fractions having R$_F$≈0.75 are combined and crystallized from diisopropyl ether. 1.1 g of the abovementioned title compound is obtained with a m.p.: 114° C.
MS: m/z=553 (M+H$^+$)
TLC: R$_F$≈0.7

Example 39

Prednisolone 17-ethyl carbonate 21-(9-fluorenylmethyl)carbonate

In the same manner as described under Example 38, 2.26 g of prednisolone 17-ethyl carbonate are reacted with 7.5 g of 9-fluorenylmethyl chloroformate, worked up and prepared. 1.7 g of the abovementioned title compound are obtained as an amorphous product (from petroleum ether).
MS: m/z=655 (M+H$^+$)
TLC: R$_F$≈0.7

Example 40

Prednisolone 17-ethyl carbonate 21-phenylacetate a) A solution of 510 mg of prednisolone 17-ethyl carbonate 21-mesylate (or an equimolar quantity of the analogous 21-p-chlorobenzene sulfonate), 145 mg of phenylacetic acid and 112 mg of triethylamine (under these circumstances, intermediary formation of the triethylammonium phenylacetate takes place) in 25 ml of dimethylformamide (or acetonitrile) are stirred at about 45° C. (oil bath) for 3 hours. After that, the dimethylformamide or acetonitrile is distilled off in vacuo and the residue is treated with 30 ml of methylene chloride. The organic phase is washed in succession with 1N aqueous hydrochloric acid and then 4 times with water. Following chromatography in accordance with Example 2b, and crystallization from diethyl ether, the abovementioned title compound is obtained having the same parameters as given under Example 2b.

b) The same title compound is arrived at if 600 mg of prednisolone 17-ethyl carbonate 21-desoxy 21-iodide, 150 mg of phenylacetic acid and 2.5 ml of triethylamine in 25 ml of acetonitrile are boiled under reflux for 45 minutes and then worked up and isolated as described under a).

c) 600 mg of prednisolone 17-ethyl carbonate 21-desoxy 21-iodide are heated at 100° C. (oil bath), while stirring, for 40 minutes together with 200 ml of potassium phenylacetate (Rhone-Poulenc) in 25 ml of absolute dimethylformamide. After that, the solution is cooled and poured into a half-saturated aqueous solution of sodium chloride, resulting in the precipitation of an oily wax, which can be filtered off and which, after filtering off, washing with water and drying (vacuum over P$_2$O$_5$), chromatography on silica gel and crystallization, yields the abovementioned title compound having the same parameters as in Examples 2a and 2b.

Example 41 ( see Ex. 13 as well )

Prednisolone 17-ethyl carbonate 21-p-methoxycinnamic ester

A solution of 2.1 g of p-methoxycinnamoyl chloride in 10 ml of absol. dioxane is added dropwise, at 0° C. and while stirring, to a solution of 3.2 g of prednisolone 17-ethyl carbonate in 20 ml of absol. pyridine. After the mixture has been stirred for from 5 to 6 h, it is poured into 500 ml of a half-saturated aqueous solution of sodium chloride and the precipitate (after standing for 48 h) is isolated using a fluted filter; this precipitate is taken up in methylene chloride and the solution is washed with water and dried using sodium sulfate, and the solvent is distilled off in vacuo. Crystallization takes place from diethyl ether/diisopropyl ether. After filtering off, 3.9 g of the abovementioned title compound are obtained with a m.p. ~197° C.

MS: m/z =593 (M+H$^+$)

TLC: R$_F$≅0.75

Where appropriate, the reaction product may be recrystallized from ethanol/diethyl ether. In the same way, 6α-methylprednisolone 17-ethyl carbonate can be used for preparing its 21-p-methoxycinnamic ester.

Preparation of the necessary p-methoxycinnamoyl chloride 25 g of p-trans-methoxycinnamic acid are stirred at 20° C. for 14 h together with 60 ml of thionyl chloride and the mixture is then boiled under reflux for 45 minutes. Excess thionyl chloride is distilled off and the remaining mixture is distilled under high vacuum at 0.2 mm Hg pressure. The yellow liquid distilling over at 125° C. solidifies on cooling and is stored over P$_2$O$_5$ in a vacuum desiccator; it can be employed in this form in reactions. Yield 26.7 g of the abovementioned reagent.

Example 42

Prednisolone 17-n-propyl carbonate 21-p-methoxycinnamic ester

In the same way as described under Example 41, 3.2 g of prednisolone 17-n-propyl carbonate are reacted with 2.1 g of p-methoxycinnamoyl chloride, followed by working-up, isolation of the title compound and its preparation in pure crystalline form (possibly also in amorphous form). 3.7 g of the abovementioned title compound are obtained.

MS: m/z=607 (M +H$^+$)

TLC: R$_F$≅0.75

In the same way, 6α-methylprednisolone 17-n-propyl carbonate can be used to prepare its 21-p-methoxycinnamic ester.

Example 43

Prednisolone 17-iso-propyl carbonate 21-p-methoxycinnamic ester

In the same way as described under Example 41, 320 mg of prednisolone 17-iso-propyl carbonate in 3 ml of absol. pyridine are reacted with 220 mg of p-methoxycinnamoyl chloride in 1 ml of absol. dioxane, followed by working-up (pouring into 100 ml of a half-saturated aqueous solution of sodium chloride), isolation of the abovementioned title compound and its preparation in pure crystalline form (possibly also in amorphous form). 310 mg of the abovementioned title compound are obtained.

MS: m/z=607 (M+H$^+$) TLC: R$_F$≅0.8

Example 44

6α-Methylprednisolone 17-ethyl carbonate 21-p-methoxycinnamic ester

In the same way as described under Example 41, 3.2 g of 6α-methylprednisolone 17-ethyl carbonate are reacted with 2.1 g of p-methoxycinnamoyl chloride, followed by working-up and preparation of the title compound in pure crystalline form (possibly also in amorphous form). 3.5 g of the abovementioned title compound are obtained.

MS: m/z=607 (M+H$^+$)

TLC: R$_F$≅0.8

Example 45

Dexamethasone 17-ethyl carbonate 21-p-methoxycinnamic ester

In the same way as described under Example 41, 3.3 g of dexamethasone 17-ethyl carbonate are reacted with 2.1 g of p-methoxycinnamoyl chloride, followed by working up, isolation of the abovementioned title compound and its preparation in pure crystalline form (possibly also in amorphous form). 3.4 g of the abovementioned title compound are obtained.

MS: m/z=625 (M+H$^+$)

TLC: R$_F$≅0.8

Example 46

Betamethasone 17-ethyl carbonate 21-p-methoxycinnamic ester

In the same way as described under Examples 41 and 43, 330 mg of betamethasone 17-ethyl carbonate in 3 ml of absol. pyridine are reacted with 220 mg of p-methoxycinnamoyl chloride in 1 ml of absol. dioxane, followed by working-up and preparation of the title compound in pure crystalline form (possibly also in amorphous form). 350 mg of the abovementioned title compound are obtained.

MS: m/z=625 (M+H$^+$)

TLC: R$_F$≅0.8

Examples 47 and 48, respectively

Prednisolone 17-iso-butyl or 17-n-butyl carbonate 21-p-methoxycinnamic ester

In the same way as described under Examples 41 and 43, 330 mg of prednisolone 17-iso-butyl or 17-n-butyl carbonate in 3 ml of absol. pyridine are reacted with 230 mg of p-methoxycinnamoyl chloride, followed by working-up, isolation of the abovementioned title compounds and their preparation in pure crystalline form (crystallized; possibly also in amorphous form). 370 mg and 330 mg, respectively, of the abovementioned title compounds are obtained.

MS: m/z=621 (M+H$^+$)

TLC: R$_F$≅0.8

Example 49 (see Ex. 41 as well)

Prednisolone 17-ethyl carbonate 21-cinnamic ester

A solution of 2.0 g of cinnamoyl chloride in 10 ml of absol. dioxane is added dropwise, at 0° C. and while stirring, to a solution of 3.2 g of prednisolone 17-ethyl carbonate in 20 ml of absol. pyridine. After the mixture has been stirred for from 5 to 6 h, it is poured into 500 ml of a half-saturated aqueous solution of sodium chloride and the precipitate (after standing for 48 h) is isolated using a fluted filter; this precipitate is taken up in methylene chloride and the solution is washed with water and dried using sodium sulfate, and the solvent is distilled off in vacuo. Crystallization takes place from diethyl ether/diisopropyl ether. After filtering off, 3.8 g of the abovementioned title compound are obtained with a m.p.~146° C.

MS: m/z=563 (M+H$^+$)

TLC: R$_F$≅0.7

Where appropriate, the reaction product may be recrystallized from ethanol/diethyl ether.

Example 50

Prednisolone 17-n-propyl carbonate 21-cinnamic ester

In the same way as described under Example 49, 3.2 g of prednisolone 17-n-propyl carbonate are reacted with 2.1 g of cinnamoyl chloride, followed by working-up, isolation of the title compound and its preparation in pure crystalline form (possibly also in amorphous form). 3.9 g of the abovementioned title compound are obtained.
  MS: m/z=577 (M+H$^+$)
  TLC: R$_f$≅0.7

Example 51

Prednisolone 17-iso-propyl carbonate 21-cinnamic ester

In the same way as described under Example 49, 320 mg of prednisolone 17-iso-propyl carbonate in 3 ml of absol. pyridine are reacted with 220 mg of cinnamoyl chloride in 1 ml of absol. dioxane, followed by working-up (pouring into 100 ml of a half-saturated aqueous solution of sodium chloride), isolation of the abovementioned title compound and its preparation in pure crystalline form (possibly also in amorphous form). 300 mg of the abovementioned title compound are obtained.
  MS: m/z=577 (M+H$^+$)
  TLC: R$_f$≅0.75

Example 52

6α-methylprednisolone 17-ethyl carbonate 21-cinnamic ester

In the same way as described under Example 49, 3.2 g of 6α-methylprednisolone 17-ethyl carbonate are reacted with 2.0 g of cinnamoyl chloride, followed by working-up and preparation of the title compound in pure crystalline form (possibly also in amorphous form). 3.6 g of the abovementioned title compound are obtained.
  MS: m/z=577 (M+H$^+$)
  TLC: R$_f$≅0.75

Example 53

Dexamethason 17-ethyl carbonate 21p-cinnamic ester

In the same way as described under Example 49, 3.3 g of dexamethasone 17-ethyl carbonate are reacted with 2.1 g of cinnamoyl chloride, following by working-up, isolation of the abovementioned title compound and its preparation in pure crystalline form (possibly also in amorphous form). 3.7 g of the abovementioned title compound are obtained.
  MS: m/z=595 (M+H$^+$)
  TLC: R$_f$≅0.75

Example 54

Betamethasone 17-ethyl carbonate 21-cinnamic ester

In the same way as described under Example 49, 330 mg of betamethasone 17-ethyl carbonate in 3 ml of absol. pyridine are reacted with 210 mg of cinnamoyl chloride in 1 ml of absol. dioxane, followed by working-up and preparation of the title compound in pure crystalline form (possibly also in amorphous form). 360 mg of the abovementioned title compound are obtained.
  MS: m/z=595 (M+H$^+$)
  TLC: R$_f$≅0.8

Examples 55 and 56, respectively

Prednisolone 17-iso-butyl or 17-n-butyl carbonate 21-cinnamic ester

In the same way as described under Example 49, 330 mg of prednisolone 17-iso-butyl or 17-n-butyl carbonate in 3 ml of absol. pyridine are reacted with 220 mg of cinnamoyl chloride, followed by working-up, isolation of the abovementioned title compounds and their preparation in pure crystalline form (possibly also in amorphous form). 370 mg and 320 mg, respectively, of the abovementioned title compounds are obtained.
  MS: m/z=591 (M+H$^+$)
  TLC: R$_f$≅0.7

Example 57 (optimization of Example 5)

Prednisolone 17-ethyl carbonate 21-cinnamic ester

A solution of 9 g of cinnamoyl chloride (trans form) in 50 ml of absol. dioxane is added dropwise, at 0° C. and while stirring, to a solution of 15 g of prednisolone 17-ethyl carbonate in 100 ml of absol. pyridine. After the mixture has been stirred at 0° C. for 4 h (TLC indicates that formation of the desired reaction product is complete), it is poured into 2 l of a half-saturated aqueous solution of sodium chloride and the crystallized precipitate is filtered off, washed with water and dried, the final time being in a vacuum desiccator. The compound is recrystallized from ethanol (e.g. dissolution in approximately 80 ml of boiling ethanol, after which the solution is allowed to cool to 20° C. and the crystals are filtered off and washed with ethanol) and, after drying, 15.0 g of the abovementioned title compound are obtained with a m.p. of 146° C. (sharper m.p. than in Example 5).
  MS: m/z=563 (M+H$^+$)
  TLC: R$_f$≅0.7

Example 58 (see Example 41 as well)

Prednisolone 17-alkyl carbonate 21-p-methoxycinnamic ester (optimized reaction mixture)

In the same way as described under Example 57, 15 g of prednisolone 17-ethyl carbonate are reacted with 10 g of p-methoxycinnamoyl chloride instead of the cinnamoyl chloride, followed by working-up and preparation in pure form by means of recrystallization. 14.9 g of the abovementioned title compound are obtained with a m.p. of 201° C.
  MS: m/z=593 (M+H$^+$)
  TLC: R$_f$≅0.75

Example 59

Prednisolone 17-ethyl carbonate 21- (3,4-methylenedioxy-)benzoate

In the same way as described under Example 41, 3 g of prednisolone 17-ethyl carbonate in 35 ml of absol. pyridine are reacted with 3.3 g of 3,4-methylenedioxybenzoyl chloride instead of the acid chloride in Example 41, followed by working-up and crystallization from diethyl ether. 3.34 g of the abovementioned title compound are obtained with a m.p. of 154° C.
  MS: m/z=581 (M+H$^+$)
  TLC: R$_f$≅0.7

Example 60

Prednisolone 17-ethyl carbonate 21- (4-phenyl) cinnamicester 84 mg of 4-dimethylaminopyridine and 1.75 g of dicyclohexylcarbodiimide are added, at 0° C. and while stirring, to a solution of 3.0 g of prednisolone 17-ethyl carbonate and 2.0 g of 4-phenylcinnamic acid in 60 ml of absol. methylene chloride. The reaction solution, which is clear at first, soon becomes turbid. After the mixture has been stirred at room temperature for about 6 hours, a TLC test no longer indicates any starting material. The mixture is then stored at +4° C. for 2 days and at −15° C. (deep freeze) for 2 days, after which the dicyclohexylurea which has precipitated out is filtered off and washed with a little methylene chloride cooled to −15° C.; the organic solvent is then stripped off from the filtrate in vacuo. The residue which remains is crystallized from boiling diethyl ether and recrystallized from ethanol/ diethyl ether. 2.0 g of the abovementioned title compound are obtained with a m.p. of 196° C.

MS: m/z=639 (M+H$^+$)
TLC: R$_f$≅0.8

Example 61

Prednisolone 17-ethyl carbonate 21- (trans-3,4-methylenedioxy)cinnamic ester

In the same way as described in Example 60, 3 g of prednisolone 17-ethyl carbonate are reacted with 2.1 g of trans-3,4-methylenedioxycinnamic acid instead of 4-phenylcinnamic acid, followed by working-up, isolation and preparation in pure form. 2.1 g of the abovementioned title compound are obtained.

MS: m/z=607 (M+H$^+$)
TLC: R$_f$≅0.8

Example 62

Prednisolone 17-ethyl carbonate 21-phenylpropiolic ester

In the same way as described in Example 60, 3 g of prednisolone 17-ethyl carbonate are reacted with 1.9 g of phenylpropiolic acid instead of 4-phenylcinnamic acid (reaction time 24 h), followed by working-up and isolation. After several weeks, the abovementioned title compound slowly crystallizes out of the resulting oil (2.4 g) in long crystals which can only be prepared in pure form with difficulty. Accurate assessment of the quantity of the oily-crystalline crude product.

MS: m/z=561 (M+H$^+$)
TLC: R$_f$≅0.8

Example 63

Prednisolone 17-ethyl carbonate 21-(5-phenylpenta-2,4-dienoic acid) ester

In the same way as described in Example 60, 3 g of prednisolone 17-ethyl carbonate are reacted with 1.56 g of 5-phenylpenta-2,4-dienoic acid (=cinnamylideneacetic acid) instead of 4-phenylcinnamic acid, followed by working-up, isolation and preparation in pure form. 3.1 g of the abovementioned title compound are obtained with a m.p. of 164° C.

MS: m/z=589 (M+H$^+$)
TLC: R$_f$≅0.8

The examples in Tables 1 and 2 below, where R(1)' is the entire side chain on the 21CH$_2$O group, are analogous to the above examples.

It was only the molecular weight peaks (m/z=... (M+H$^+$)), obtained from the mass spectra, which were in each case evaluated (as oil or wax or inamorphous form or crystallized) for characterizing the synthesis products, and this was not, as a rule, followed by any purification by crystallization (recrystallization) or chromatography.

TABLE 1

Basic corticoid: Prednisolone

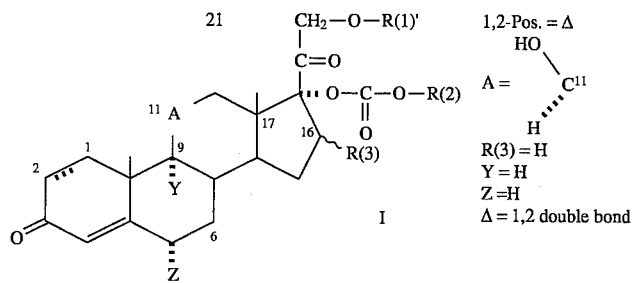

| Run No. | Carboxylic acid Carbonyl chloride or Carboxylic anhydride employed | Process variant according to example | R(2) | R(1)' | MS (m/z) (M + H$^+$) |
|---|---|---|---|---|---|
| 1.1 | Cl—⟨C$_6$H$_4$⟩—COCl | 1a, 1b, 13 | —C$_2$H$_5$ | Cl—⟨C$_6$H$_4$⟩—CO— | 572 |
| 1.2 | O$_2$N—⟨C$_6$H$_4$⟩—COCl | 1a, 1b, 13 | —C$_2$H$_5$ | O$_2$N—⟨C$_6$H$_4$⟩—CO— | 582 |
| 1.3 | CH$_3$CONH—⟨C$_6$H$_4$⟩—COCl | 1a, 1b, 13 | —C$_2$H$_5$ | CH$_3$CONH—⟨C$_6$H$_4$⟩—CO— | 594 |

TABLE 1-continued

Basic corticoid: Prednisolone $A = \begin{matrix} HO \\ H \end{matrix} C^{11}$

R(3) = H
Y = H
Z = H
Δ = 1,2 double bond

| Run No. | Carboxylic acid Carbonyl chloride or Carboxylic anhydride employed | Process variant according to example | R(2) | R(1)' | MS (m/z) (M + H⁺) |
|---|---|---|---|---|---|
| 1.4 | 2-(OCOCH₃)-C₆H₄-CO₂H | 2b, 29, 30, 31 | —C₂H₅ | 2-(OCOCH₃)-C₆H₄-CO— | 595 |
| 1.5 | 4-(CH₃S)-C₆H₄-CO₂H | 2b, 29, 30, 31 | —C₂H₅ | 4-(CH₃S)-C₆H₄-CO— | 583 |
| 1.6 | C₆H₅-SCH₂CO₂H | 2b, 29, 30, 31 | —C₂H₅ | C₆H₅-SCH₂CO— | 583 |
| 1.7 | C₆H₅-(CH₂)₃CO₂H | 2b, 29, 30, 31 | —C₂H₅ | C₆H₅-(CH₂)₃CO— | 579 |
| 1.8 | 2-pyridyl-CO₂H | 2b, 29, 30, 31 | —C₂H₅ | 2-pyridyl-CO— | 538 |
| 1.9 | pyridine-2,x-dicarboxylic acid | 2b, 29, 30, 31 (2 equ. corticoid) | —C₂H₅ | pyridine-2,x-di-CO— (dimer) | 997 (996.5) |
| 1.10 | 4-CH₃-C₆H₄-COCl (p-isomer) | 1a, 1b, 6, 13 | —C₂H₅ | 4-CH₃-C₆H₄-CO— (p-isomer) | 551 |
| 1.11 | o-isomer | 1a, 1b, 6 | —C₂H₅ | o-isomer | 551 |
| 1.12 | 3-CH₃-C₆H₄-CO₂H | 2b, 29, 30 | —C₂H₅ | 3-CH₃-C₆H₄-CO— | 551 |
| 1.13 | 3-CH₃-C₆H₄-CO₂H | 2b, 29, 30 | n-C₃H₇ | 3-CH₃-C₆H₄-CO— | 565 |

TABLE 1-continued

Basic corticoid: Prednisolone

[Structure I: Prednisolone-based steroid with substituents at position 21 (CH₂—O—R(1)'), C=O, 17-position O—C(=O)—O—R(2), 16-position R(3); 1,2-Pos. = Δ; A = HO—C11(H); R(3) = H; Y = H; Z = H; Δ = 1,2 double bond]

| Run No. | Carboxylic acid Carbonyl chloride or Carboxylic anhydride employed | Process variant according to example | R(2) | R(1)' | MS (m/z) (M + H⁺) |
|---|---|---|---|---|---|
| 1.14 | 3-pyridyl-CH₂CO₂H | 2b, 29, 30, 31 | —C₂H₅ | 3-pyridyl-CH₂CO— | 552 |
| 1.15 | 3-pyridyl-CH=CH—CO₂H | 2b, 29, 30, 31 | —C₂H₅ | 3-pyridyl-CH=CH—CO— | 564 |

TABLE 2

Basic Corticoid: Prednisolone

[Structure I: same as above; R(3) = H; Y = H; Z = H; Δ = 1,2 double bond]

| Run No. | Carboxylic acid Carbonyl chloride or Carboxylic anhydride employed | Process variant according to example | R(2) | R(1)' | MS (m/z) (M + H⁺) |
|---|---|---|---|---|---|
| 2.1 | 3-thienyl-COCl | 1a, 13 | —C₂H₅ | 3-thienyl-CO— | 543 |
| 2.2 | 3-thienyl-CH₂CO₂H | 2b, 29, 30, 31 | —C₂H₅ | 3-thienyl-CH₂CO— | 557 |
| 2.3 | 2-thienyl-CH₂CH₂COCl | 1a, 1b, 13 | —C₂H₅ | 2-thienyl-CH₂CH₂CO— | 571 |
| 2.4 | 5-chloro-2-thienyl-COCl | 1a, 1b, 13 | —C₂H₅ | 5-chloro-2-thienyl-CO— | 578.5 |

TABLE 2-continued
Basic Corticoid: Prednisolone
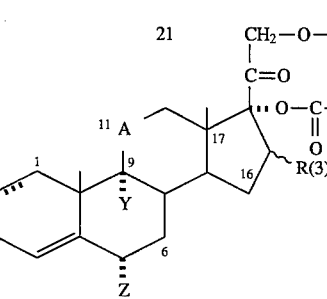
$A =$ structure with HO and $C^{11}$
R(3) = H
Y = H
Z = H
Δ = 1,2 double bond
| Run No. | Carboxylic acid Carbonyl chloride or Carboxylic anhydride employed | Process variant according to example | R(2) | R(1)' | MS (m/z) (M + H$^+$) |
|---|---|---|---|---|---|
| 2.5 | 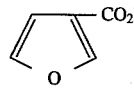 | 2b, 29, 30, 31 | —C$_2$H$_5$ | 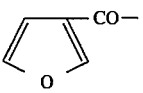 | 527 |
| 2.6 | 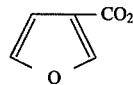 | 2b, 29, 30, 31 | n-C$_3$H$_7$ | 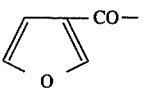 | 541 |
| 2.7 | 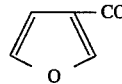 | 2b, 29, 30, 31 | n-C$_4$H$_9$ | 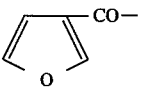 | 555 |
| 2.8 | 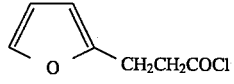 | 1a, 1b, 13 | —C$_2$H$_5$ | 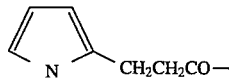 | 555 |
| 2.9 | 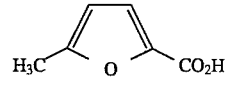 | 2b, 29, 30, 31 | —C$_2$H$_5$ | 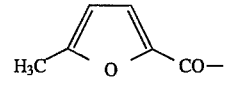 | 541 |
| 2.10 | 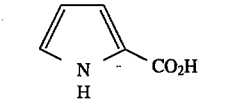 | 2b, 29, 30, 31 | —C$_2$H$_5$ | 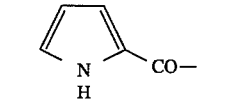 | 526 |
| 2.11 | 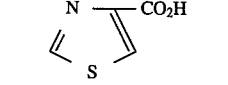 | 2b, 29, 30 | —C$_2$H$_5$ | 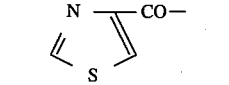 | 544 |
| 2.12 | 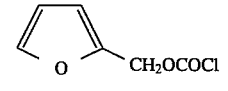 | 1b, 13 | —C$_2$H$_5$ | 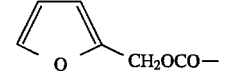 | 557 |
| 2.13 | 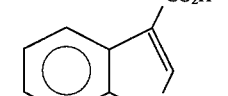 | 2b, 29, 30, 31 | —C$_2$H$_5$ | 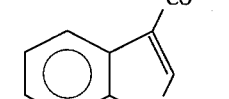 | 576 |
| 2.14 | 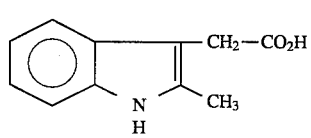 | 2b, 29, 30, 31 | —C$_2$H$_5$ | 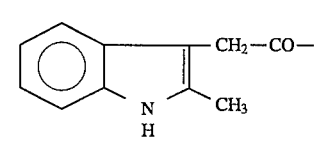 | 604 |

TABLE 2-continued
Basic Corticoid: Prednisolone
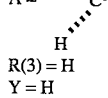
| Run No. | Carboxylic acid Carbonyl chloride or Carboxylic anhydride employed | Process variant according to example | R(2) | R(1)' | MS (m/z) (M + H+) |
|---|---|---|---|---|---|
| 2.15 | 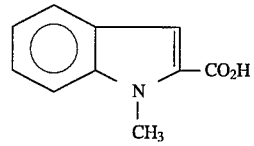 | 2b, 29, 30, 31 | —C$_2$H$_5$ | 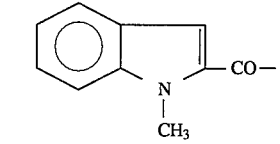 | 590 |
| 2.16 | 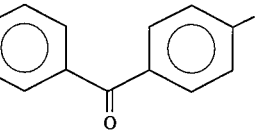 | 2b, 29, 30 | —C$_2$H$_5$ | 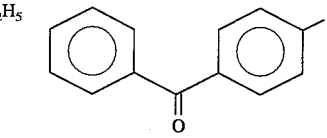 | 641 |
| 2.17 | 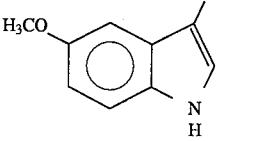 | 2b, 29, 30, 31 | —C$_2$H$_5$ | 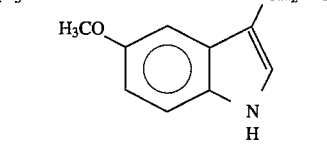 | 620 |
| 2.18 | 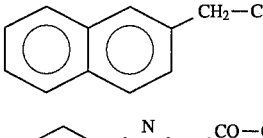 | 2b, 29, 30, 31 | —C$_2$H$_5$ | 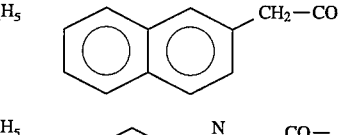 | 601 |
| 2.19 | 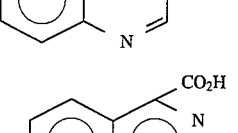 | 1a, 1b, 13 | —C$_2$H$_5$ | 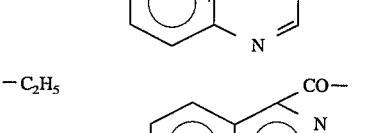 | 589 |
| 2.20 | 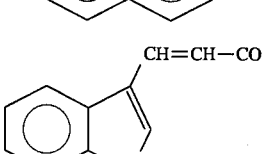 | 2b, 29, 30, 31 | —C$_2$H$_5$ | 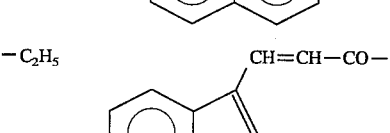 | 588 |
| 2.21 | 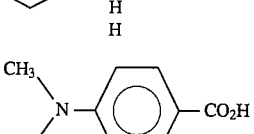 | 2b, 29, 30, 31 | —C$_2$H$_5$ | 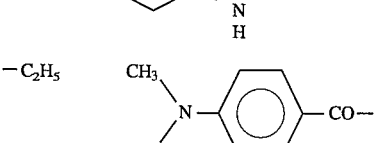 | 602 |
| 2.22 |  | 2b, 29, 30, 31 | —C$_2$H$_5$ |  | 580 |

LIST 2

A) The following carboxylic acids of the formula IV, or their activated derivatives, are examples of suitable starting compounds:

1. Benzoic acids and derivatives

Benzoic acid; 2-, 3- or 4-methoxybenzoic acid; 2-, 3- or 4-chlorobenzoic acid; bromo- or iodobenzoic acid; fluorobenzoic acid; 2,4-, 3,4- or 2,6-difluoro- or dichlorobenzoic acid; 2-, 3- or 4-methylbenzoic acid; 3,5-dimethylbenzoic acid; 3- or 4-trifluorobenzoic acid; 4-cyanobenzoic acid, phthalaldehydic acid, terephthalaldehydic acid, phthalic acid, terephthalic acid, 4-acetaminobenzoic acid, 4-acetaminomethylbenzoic acid, 2-, 3- or 4-nitrobenzoic acid; 2-methoxy-4-nitrobenzoic acid, acetylsalicylic acid; 3,5-diacetoxybenzoic acid, 4-tert-butoxybenzoic acid; 4-tertbutylbenzoic acid; 3,4-methylenedioxybenzoic acid; 2,3-, 3,5- or 2,6-dimethoxybenzoic acid; 2,3,4-trimethoxybenzoic acid; 4-formaminobenzoic acid; 4-BOC-aminobenzoic acid; 4-mercaptomethylbenzoic acid; 4-phenylbenzoic acid, 4-benzylbenzoic acid, 4-phenylcarbonylbenzoic acid; 4-phenoxybenzoic acid; benzophenone-4- or 3- or 2-carboxylic acid; tiaprofenic acid; 5-tert-butylisophthalic acid; aminobenzoic acids, in particular 4-(dimethylamino)benzoic acid;

2. Heteroaromatic carboxylic acids

2-, 3- or 4-pyridinecarboxylic acid; nicotinic acid; 2-mercaptomethylnicotinic acid; 2-chloronicotinic acid, 2-fluoronicotinic acid; 6-methoxynicotinic acid; 6-chloronicotinic acid; 6-acetamidonicotinic acid; pyridine-2,6-dicarboxylic acid;pyrazine-2-carboxylic acid; 6,6'-dithiodinicotinic acid; thiophene-2- or -3-carboxylic acid; 5- or 4-methylthiophene-2- or -3-carboxylic acid; 5- or 4-chlorothiophene-2- or -3-carboxylic acid; furan-2- or -3-carboxylic acid; 5-chlorofuran-2-carboxylic acid; 5-methylfuran-2-carboxylic acid; 5-nitrofuran-2-carboxylic acid, furan-2,5-dicarboxylic acid; pyrrole-2-carboxylic acid; imidazole-2-carboxylic acid; 3-isopropoxythiophene-5-carboxylic acid; 5-chlorothiophene-2-carboxylic acid;

2-, 3- or 4-methoxynicotinic acid;

3. Arylacetic and hetarylacetic acids and analogs and/or homologs a.) Non-fused acids Phenylacetic acid; 2-methyl- or 3-methyl- or 4-methylphenylacetic acid, 4-tert-butylphenylacetic acid; 2-chloro- or 3-chloro- or 4-chlorophenylacetic acid; 2,6-dichloro- or 3,4-dichlorophenylacetic acid; 2-fluoro- or 3-fluoro- or 4-fluorophenylacetic acid; 2,6-difluorophenylacetic acid; 2-nitro- or 3-nitro- or 4-nitrophenylacetic acid; 2,4-dinitrophenylacetic acid; 2-methoxy- or 3-methoxy- or 4-methoxyphenylacetic acid; 4-benzyloxyphenylacetic acid; 3-chloro-4-methoxyphenylacetic acid; 3-bromo-4-methoxyphenylacetic acid; 3-nitro-4-methoxyphenylacetic acid; 3,4-dimethoxyphenylacetic acid; 2,3,4-trimethoxyphenylacetic acid; 3,4-methylenedioxyphenylacetic acid; 3,4-diethoxyphenylacetic acid; 4-biphenylacetic acid; 3-phenoxyphenylacetic acid; 2-acetamino- or 3-acetamino- or 4-acetaminophenylacetic acid; 3-(N)-BOC-aminophenylacetic acid; 4-formylaminophenylacetic acid; 4-N,N-dimethylaminophenylacetic acid;

4-Benzyloxyphenylacetic acid; 4-(2-methoxybenzyloxy)phenylacetic acid; 4-(4-fluorobenzyloxy)phenylacetic acid; 2-(thiazol-4-yl)acetic acid; 2-(thiazol- 4-yl)-2-methoxyiminoacetic acid; 3-phenylpropionic acid; D,L-2-phenylpropionic acid; 3-[4methylphenyl]propionic acid, 3-[4-chloro- or 4-fluoro-or 4-methoxyphenyl]propionic acids; (S)-(+)-2-phenylpropionic acid; (R)-(−)-2-phenylpropionic acid; 4-phenylbutyric acid; phenoxyacetic acid and derivatives (substituents in the phenyl moiety); cis- or (preferred) trans-cinnamic acid; 2-, 3- or 4-methoxycinnamic acid; 4-ethoxycinnamic acid; 3,4-dimethoxycinnamic acid; 3,4,5-trimethoxycinnamic acid; 4-fluorocinnamic acid; 3- or 4-chlorocinnamic acid; 3-bromocinnamic acid; 2- or 3-nitrocinnamic acid; 4-cyanocinnamic acid; 4-isopropylcinnamic acid; 4-tert-butylcinnamic acid, 2- or 4-trifluoromethylcinnamic acid; D,L- or (S)- or (R)-2-(4-isobutylphenyl)propionic acid (Ibuprofen); 4-(isobutylphenyl)acetic acid (Ibufenac); phenylmercaptoacetic acid; phenylpropiolic acid; 2-methyl-3-(4-tetradecyloxyphenyl)-2-propenoic acid (MTPA); 3-(4-crotyloxyphenyl)propionic acid; 4-dodecylbenzoylacetic acid (DBAA); benzoylacrylic acid; chlorambucil; 3,4,5-trimethoxybenzoylacrylic acid; 2-(4-(thiazol-2yl)phenyl)propionic acid; 2-(xanthonoxy)acetic acid; 2-phenylcyclopropane-carboxylic acids (trans); 3-(phenylmercapto)acrylic acid; (4-phenyl)butyric acid;

2-thienylacetic acid; 3-thienylacetic acid; N-methylpyrrole-2-carboxylic acid; furylacetic acid; 2-, 3- or 4-pyridylacetic acid;

3-(2-Furyl)acrylic acid; 3-(2-thienyl)acrylic acid; 3-(3-thienyl)acrylic acid; 3-(4- or 2-pyridyl)acrylic acid; 3-(2-thienyl)propionic acids; 3-(2-furyl)propionic acid; 3-(4-imidazolyl)acrylic acid; (N-methylpyrrol-2-yl)acetic acid;

b.) Fused acids

Indole-2-carboxylic acid; indole-3-carboxylic acid; indole-4-carboxylic acid; (N-methyl)indole-2-carboxylic acid; 2- or 1-naphthalenecarboxylic acid; 2- or 3- or 4-quinolinecarboxylic acid; xanthene-α-carboxylic acid; 1-fluorenecarboxylic acid; 9-fluorenone-4-carboxylic acid;

3-Indolylacetic acid; 2-indolylacetic acid; (N-methyl)-2- or -3-indolylacetic acid; 3-(3-indolyl)propionic acid; 3- or 2-indolylacrylic acid (also (N-methyl)); (2-methyl-3-indolyl)acetic acid, 3,4(methylenedioxy)phenylacetic acid; 3,4-(methylenedioxy)cinnamic acid; indole-3-butyric acid; (5-methoxyindol-3-yl)acetic acid; naphthyl-1- or -2-acetic acid; pyrazine-2-carboxylic acid; flavone-8-acetic acid; 5,6-dimethylxanthone-4-acetic acid (L. L. Thomsen et al.: Cancer Chemother, Pharmacol. 31, 151ff. (1992) demonstrate that the corticoid 21-carboxylic esters prepared from this could also have an antitumorigenic effect).

B) The following chloroformic esters (haloformates) of the formula III are examples of suitable starting compounds:

phenyl chloroformate

Benzyl chloroformate

4-Bromophenyl chloroformate

α-Chloro-2-fluorobenzyl chloroformate

4-Chlorophenyl chloroformate (+) or (−)- 1-(9-fluorenyl)ethyl chloroformate

9-Fluorenylmethyl chloroformate

4-Fluorophenyl chloroformate

4-Methoxyphenyl chloroformate

2-Nitrophenyl chloroformate p-Tolyl chloroformate

Mono- or bis-chloroformic esters of 1.): 2,5-bis(hydroxymethyl) furan and of 2.): 2,6-bis-(hydroxymethyl)pyridine Chloroformic esters of 2-hydroxymethylfuran

We claim:

1. A corticoid 17-alkyl carbonate 21-carboxylic or carbonic ester of the formula I

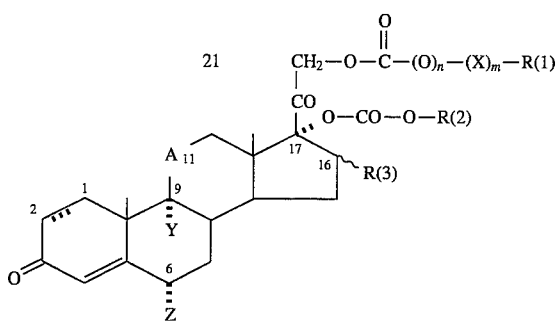

in which:

A is CHOH and CHCl in arbitrary steric arrangement, CH$_2$, C=O or 9(11) double bond;

Y is hydrogen, fluorine or chlorine;

Z is hydrogen, fluorine or methyl;

R(1) is optionally substituted aryl, arylalkyl, arylthioalkyl, pyridyl, pyridylalkyl, thienyl, thienylalkyl, furyl, furylalkyl, pyrrolyl, thiazolyl, indolyl, indolylalkyl, quinoxalinyl and isoquinolinyl;

X is (C$_1$–C$_4$)-aliphatic hydrocarbon, saturated, unsaturated once or more than once, branched by alkyl groups, or is (C$_1$–C$_4$)-hydrocarbon, unsubstituted or inserted or substituted by heteroatoms O, S or N;

n is zero or 1;

m is zero or 1;

R(2) is linear or branched (C$_1$–C$_8$)-alkyl or —(CH$_2$)$_2$—OCH$_3$; and

R(3) is hydrogen or α- or β-methyl.

2. A corticoid 17alkyl carbonate 21-carboxylic or carbonic ester I as claimed in claim 1, wherein R(1), A, Y, Z, R(3) and R(4) are defined as in claim 1, and wherein R(2) is linear or branched (C$_1$–C$_5$)-alkyl or —(CH$_2$)$_2$—OCH$_3$.

3. A pharmaceutical composition for treating inflammatory or allergic dermatoses comprising an effective amount of a compound I as claimed in claim 11 and a pharmaceutically acceptable carrier.

4. A method for treating dermatoses, which comprises applying to the affected skin an effective amount of a compound I as claimed in claim 1 in combination with a pharmaceutically acceptable carrier.

* * * * *

UNITED STATES PATENT AND TRADEMARK OFFICE
CERTIFICATE OF CORRECTION

PATENT NO. : 5,608,093
DATED : March 04, 1997
INVENTOR(S) : Ulrich STACHE et al.

It is certified that error appears in the above-indentified patent and that said Letters Patent is hereby corrected as shown below:

In the Abstract item [57], (in formula III) --(X)-- should read --$(X)_m$--

Claim 2, column, 40, line 10, "17alkyl" should read --17-alkyl--.

Claim 3, column 40, line 16, "claim 11" should read --claim 1--.

Signed and Sealed this

Tenth Day of February, 1998

Attest:

BRUCE LEHMAN

Attesting Officer     Commissioner of Patents and Trademarks